(12) United States Patent
Plahey et al.

(10) Patent No.: US 11,717,600 B2
(45) Date of Patent: Aug. 8, 2023

(54) ADMINISTERING DIALYSIS TREATMENT USING A HYBRID AUTOMATED PERITONEAL DIALYSIS SYSTEM

(71) Applicant: Fresenius Medical Care Holdings, Inc., Waltham, MA (US)

(72) Inventors: Kulwinder Plahey, Martinez, CA (US); James Peterson, Benicia, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 419 days.

(21) Appl. No.: 16/893,241

(22) Filed: Jun. 4, 2020

(65) Prior Publication Data
US 2021/0379259 A1    Dec. 9, 2021

(51) Int. Cl.
    *A61M 1/28*      (2006.01)
    *A61M 60/40*     (2021.01)
    *A61M 60/258*    (2021.01)
    *A61M 60/279*    (2021.01)

(52) U.S. Cl.
CPC ............ *A61M 1/282* (2014.02); *A61M 1/287* (2013.01); *A61M 60/258* (2021.01); *A61M 60/279* (2021.01); *A61M 60/40* (2021.01); *A61M 2205/128* (2013.01); *A61M 2205/18* (2013.01);
(Continued)

(58) Field of Classification Search
CPC ........ A61M 1/28; A61M 1/282; A61M 1/287; A61M 2205/121; A61M 2205/128; A61M 2205/18; A61M 2205/3331; A61M 2205/3334; A61M 2205/3379;
(Continued)

(56) References Cited

U.S. PATENT DOCUMENTS

| | | |
|---|---|---|
| 5,004,459 A | 4/1991 | Peabody et al. |
| 5,141,493 A | 8/1992 | Jacobson et al. |
| 5,670,057 A | 9/1997 | Chen et al. |

(Continued)

FOREIGN PATENT DOCUMENTS

| | | |
|---|---|---|
| EP | 2 398 529 A1 | 12/2011 |
| EP | 3 403 678 A1 | 11/2018 |

(Continued)

OTHER PUBLICATIONS

International Patent Application No. PCT/US2021/024116, Search Report (dated Jun. 23, 2021).

*Primary Examiner* — Dirk R Bass
(74) *Attorney, Agent, or Firm* — Leydig, Voit & Mayer, Ltd.

(57) ABSTRACT

A dialysis machine (e.g., a peritoneal dialysis (PD) machine) can include a control unit configured to operate in a hybrid automated mode during a PD treatment. A processor in the control unit is configured to engage a pump during a fill phase of the PD cycle. The volume of fluid (e.g., dialysate) transferred to a patient line during the fill phase is monitored. After a dwell period, the pump is disengaged at the start of a drain phase of the PD cycle. Disengaging the pump can include: configuring valves of a disposable cassette to bypass the pump chambers of a disposable cassette; activating a bypass valve to shunt the patient line to a drain line; or moving a roller assembly of a peristaltic pump. The fluid transferred from the patient line to the drain line is monitored during the drain phase of the PD cycle.

22 Claims, 18 Drawing Sheets

(52) U.S. Cl.
CPC ............... *A61M 2205/3331* (2013.01); *A61M 2205/3379* (2013.01)

(58) Field of Classification Search
CPC ........ A61M 2205/3393; A61M 60/258; A61M 60/279; A61M 60/40
See application file for complete search history.

(56) References Cited

U.S. PATENT DOCUMENTS

| | | |
|---|---|---|
| 6,196,992 B1 | 3/2001 | Keilman et al. |
| 6,228,047 B1 | 5/2001 | Dadson |
| 2003/0217962 A1 | 11/2003 | Childers et al. |
| 2005/0209563 A1 | 9/2005 | Hopping et al. |
| 2009/0113335 A1 | 4/2009 | Sandoe et al. |
| 2010/0217180 A1* | 8/2010 | Akonur ................. A61M 1/282 703/2 |
| 2017/0203023 A1 | 7/2017 | Farrell et al. |
| 2017/0368249 A1* | 12/2017 | Bourne ................... A61M 1/28 |

FOREIGN PATENT DOCUMENTS

| | | |
|---|---|---|
| WO | WO 99/006082 A1 | 2/1999 |
| WO | WO 2016/095026 A1 | 6/2016 |
| WO | WO 2018/210904 A1 | 11/2018 |

* cited by examiner

ADMINISTERING DIALYSIS TREATMENT USING A HYBRID AUTOMATED PERITONEAL DIALYSIS SYSTEM

BACKGROUND

Dialysis is a treatment used to support a patient with insufficient renal function. The two principal treatment options are hemodialysis (HD) and peritoneal dialysis (PD). During hemodialysis, the patient's blood is removed, e.g., via an arteriovenous (AV) fistula or other methods (e.g., AV graft), and passed through a dialyzer of a dialysis machine while also passing a dialysis solution, referred to as dialysate, through the dialyzer. A semi-permeable membrane in the dialyzer separates the blood from the dialysate within the dialyzer and facilitates the exchange of waste products (e.g., urea, creatine, potassium, etc.) between the blood stream and the dialysate. The membrane prevents the transfer of blood cells, protein, and other important components in the blood stream from entering the dialysate solution. The cleaned blood stream is then returned to the patient's body. In this way, the dialysis machine functions as an artificial kidney for cleaning the blood in patients with insufficient renal function.

In contrast with hemodialysis, the peritoneal dialysis treatment option introduces dialysate into a patient's peritoneal cavity, which is an area in the abdomen between the parietal peritoneum and visceral peritoneum (e.g., a space between the membrane that surrounds the abdominal wall and the membranes that surround the internal organs in the abdomen). The lining of the patient's peritoneum functions as a semi-permeable membrane that facilitates the exchange of waste product between the bloodstream and the dialysate, similar in function to the membrane in the dialyzer of the hemodialysis machine. The patient's peritoneal cavity is drained and filled with new dialysate over a number of PD cycles. Peritoneal dialysis can be performed using either gravity or an automated pumping mechanism to fill and drain the abdomen during a PD cycle.

Automated PD machines, sometimes referred to as PD cyclers, are designed to control the PD treatment process so that it can be performed at home without clinical staff, typically while the patient sleeps overnight so as to minimize interference with the patient's life. The process is referred to as continuous cycler-assisted peritoneal dialysis (CCPD). Many PD cyclers are designed to automatically infuse, dwell, and drain dialysate to and from the peritoneal cavity. The PD treatment typically lasts several hours, often beginning with an initial drain phase to empty the peritoneal cavity of used or spent dialysate that was left in the peritoneal cavity at the end of the last PD treatment. The sequence then proceeds through a progression of fill, dwell, and drain phases that follow sequentially. A group of fill, dwell, and drain phases, in order, can be referred to as a PD cycle.

Automated PD machines conventionally use a pump to both fill and drain the patient. One of the common complaints during PD treatment is related to drain complications. The patient's peritoneum is a biological system that is complex and unique to each patient. Depending on the morphology of the patient's peritoneal cavity, the location of the catheter in the abdomen during treatment, interference by the omentum blocking the orifices in the catheter, and changes due to intestinal filling, constipation, etc. can cause issues with drainage. These problems can be exasperated by a negative pressure in the patient line caused by the pump operation. For example, a negative pressure in the patient line can cause suction of a tissue against the catheter that prevents fluid from being able to drain into the catheter. The fill cycle does not have the same issues with blockage of the catheter or foreign debris clogging the patient line due to the positive pressure caused by clean dialysate being pumped into the patient line by the PD cycler.

SUMMARY

A hybrid automated PD system is provided for performing a PD treatment. The PD system can include a pump, one or more sensors for measuring a volume of transferred fluid, and a processor. The processor is configured to engage the pump during a fill phase of a PD cycle and disengage the pump during a drain phase of the PD cycle. A patient line is shunted to a drain line to allow fluid to bypass the pump during the drain phase of the PD cycle.

In an embodiment, the pump comprises one or more pistons configured to engage with one or more corresponding pump chambers formed in a disposable cassette connected to the patient line and the drain line. Disengaging the pump comprises configuring one or more valves of the cassette to form a fluid path in the cassette that connects the patient line to the drain line. The fluid path does not include any of the one or more pump chambers.

In an embodiment, the pump comprises a peristaltic pump. Disengaging the pump comprises moving a roller assembly away from a fixed surface such that a flexible tube between the roller assembly and the fixed surface is not contacted by the roller assembly.

In some embodiments, disengaging the pump comprises opening a bypass valve to allow fluid to flow from the patient line to the drain line.

In some embodiments, the one or more sensors comprise a flow meter. In other embodiments, the one or more sensors comprise at least two pressure transducers configured to measure a pressure differential across a fixed length of tubing. In yet other embodiments, the one or more sensors comprise load cells for measuring a weight of the fluid to indirectly derive a volume of fluid flowing through the patient line.

In some embodiments, the processor is further configured to: monitor, based on signals from the one or more sensors, an amount of fluid transferred to a patient line during the fill phase; monitor, based on signals from the one or more flow sensors, an amount of fluid transferred from the patient line to the drain line during the drain phase; and generate an alert when a difference in the amount of fluid transferred to the patient line during the fill phase and the amount of fluid transferred from the patient line to the drain line during the drain phase is above a threshold value. In an embodiment, the processor is further configured to disengage the pump responsive to the alert.

In some embodiments, a method for operating a hybrid automated PD machine is performed by engaging a pump during a fill phase of a PD cycle; monitoring, using one or more flow sensors, an amount of fluid transferred to a patient line during the fill phase; disengaging the pump after a dwell period has elapsed to begin a drain phase of the PD cycle; and monitoring, using the one or more flow sensors, an amount of fluid transferred from the patient line to the drain line during the drain phase. The patient line is shunted to a drain line to allow fluid to bypass the pump during the drain phase of the PD cycle. A non-transitory computer readable storage medium storing instructions for performing the method above is also disclosed.

DETAILED DESCRIPTION

A peritoneal dialysis (PD) machine can be designed to operate a hybrid PD cycle. In the hybrid PD cycle, the PD machine infuses dialysate into a patient using a pump. In other words, the fluid is pumped into the patient line creating a positive fluid pressure in the patient line that aids in moving fluid into the patient's abdominal cavity. Once the patient's abdominal cavity has the prescribed amount of fluid, the PD cycle enters a dwell period where waste is exchanged across the patient's peritoneum. After a dwell period is complete, the PD cycle enters a drain phase where fluid is allowed to drain from the patient's abdominal cavity. Unlike conventional PD cyclers that utilize the pump during both the fill and drain phases, the hybrid automated PD machine provides the option to disengage the pump during the drain phase to allow the effluent to drain naturally from the patient's abdominal cavity.

In some embodiments, the pump is a peristaltic pump that can be actively disengaged from the fluid path in order to allow the fluid to flow naturally from the patient to the drain. In some embodiments, the action of the natural flow may be due to gravity and/or may be due to a pressure difference between the proximate end of the patient line connected to the catheter in the patient's abdomen and a distal end of the patient line connected to a drain. In some embodiments, the pump is disengaged by opening valves that allow the fluid to bypass the pump rather than disengaging the pump from the fluid path. For example, a piston-type pump utilized with a disposable cassette can be disengaged by using a bypass valve that opens a direct path between a patient line connected to the cassette and a drain line connected to the cassette. In yet another embodiment, a separate bypass valve that is external to the cassette can be utilized to shunt the patient line and the drain line, thereby bypassing the cassette entirely during the drain phase. The external bypass valve can be useful to decrease the resistance to fluid flow that could be introduced by small cavities in the cassette utilized by the bypass fluid path.

It will be appreciated that conventional PD cyclers may utilize the pump to accurately monitor the amount of fluid that is introduced to or drained from the patient's abdomen. Accurately monitoring the fluid is necessary to ensure the safety of the patient and to avoid overfilling the patient with an excess of dialysate. Disengaging the pump can frustrate the ability to accurately monitor the amount of fluid being drained from the patient during the drain phase of the PD cycle. In some embodiments, fluid flow sensors are introduced to monitor the amount of fluid that flows into or is drained from the patient line. The fluid flow sensors can include an ultrasonic fluid flow sensor or a pair of pressure transducers.

Figure 1:
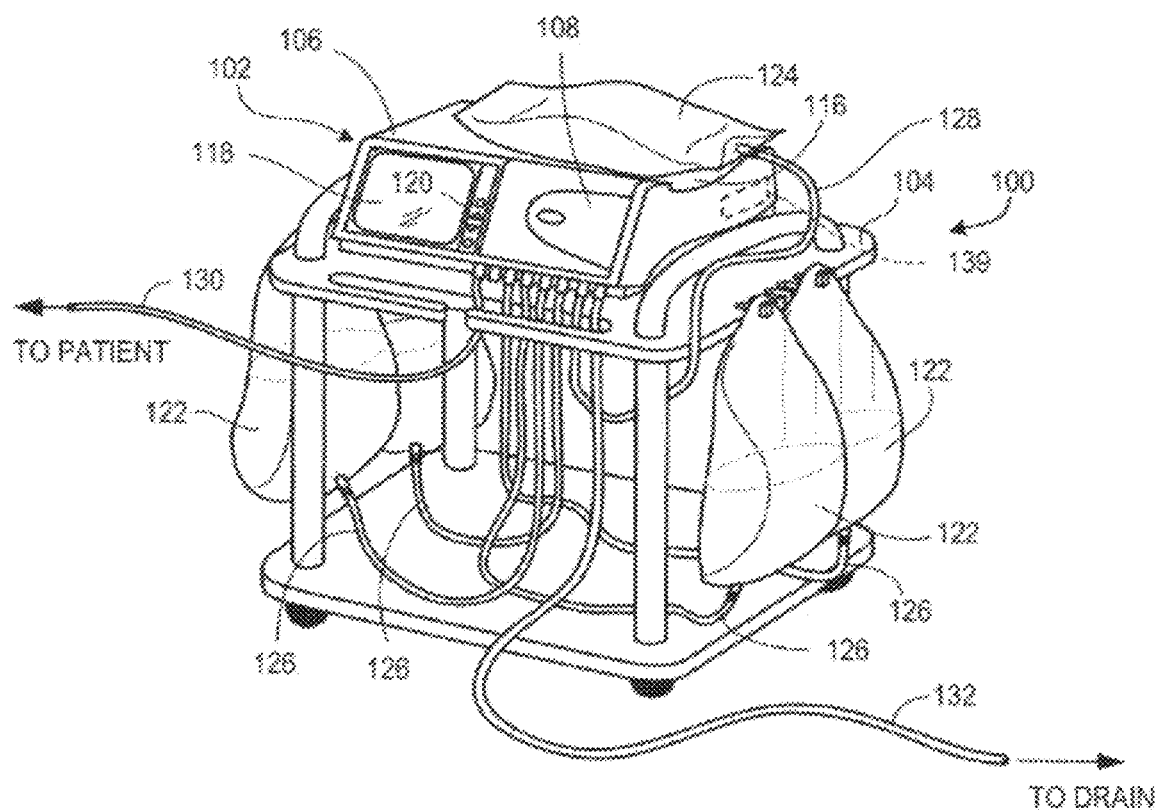
FIG. 1 illustrates a peritoneal dialysis (PD) system, in accordance with some embodiments.

FIG. 1 illustrates a peritoneal dialysis (PD) system 100, in accordance with some embodiments. The PD system 100 can include a PD machine 102, which can alternately be referred to as a PD cycler, seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. The cassette compartment 114, cassette interface 110, and cassette 112 are shown in more detail in FIG. 2. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bags 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The catheter may be surgically implanted in the patient and connected to the patient line 130 via a port, such as a fitting, prior to the PD treatment. The drain line 132 can be connected to a drain or drain receptacle and can be used to pass dialysate from the cassette 112 to the drain or drain receptacle during use.

The PD machine 102 also includes a control unit 139 (e.g., a processor, controller, system-on-chip (SoC), or the like). The control unit 139 can receive signals from and transmit signals to the touch screen display 118, the control panel 120, and the various other components of the PD system 100. The control unit 139 can control the operating parameters of the PD machine 102. In some embodiments, the control unit 139 includes an MPC823 PowerPC device manufactured by Motorola, Inc. As further discussed in detail elsewhere herein, in some embodiments, the control unit 139 may be configured to control disengaging and/or bypassing of a pump in connection with naturally draining the dialysate from a patient during the drain phase of a PD cycle.

Figure 2:
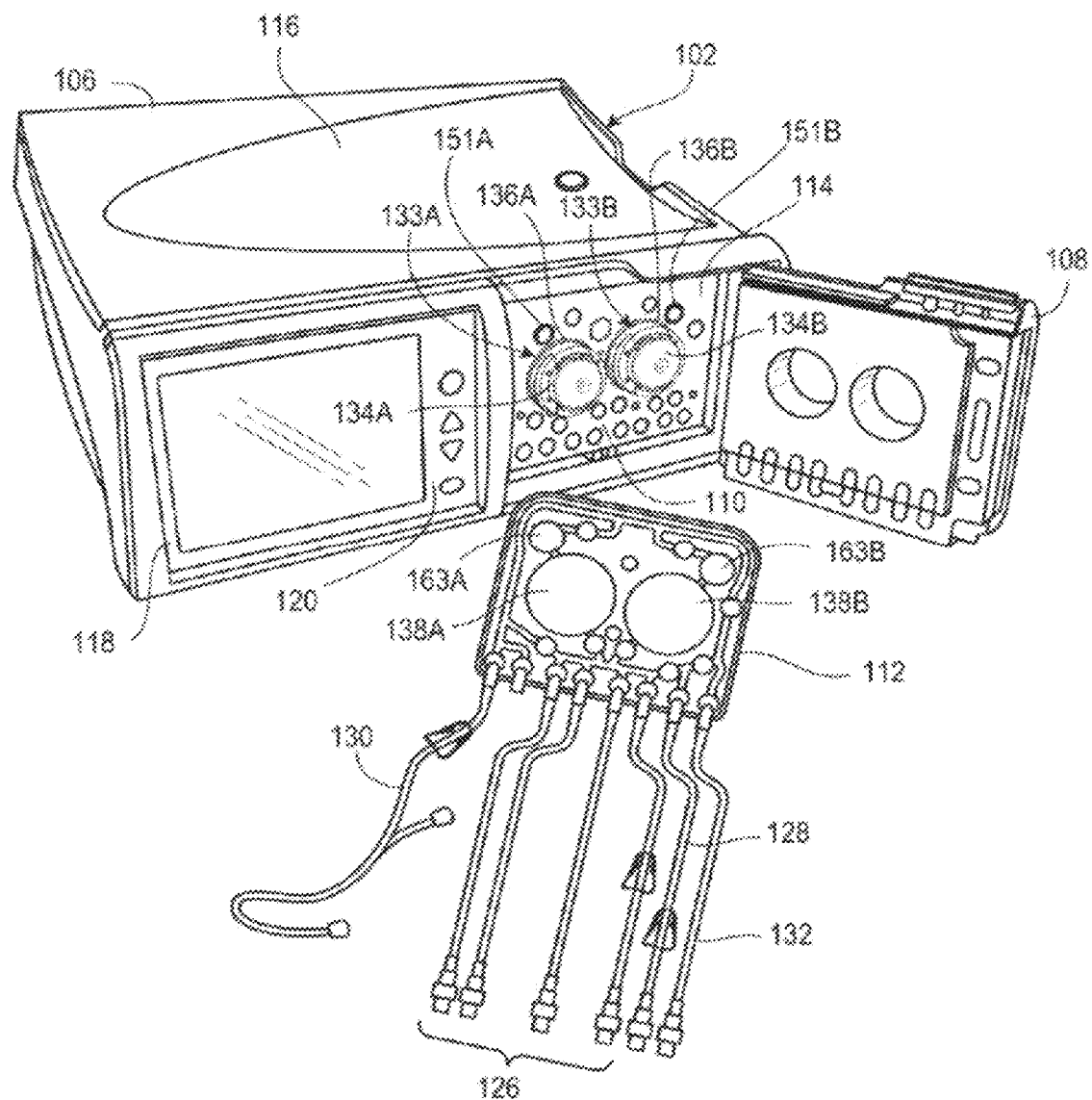
FIG. 2 is a perspective view of the PD machine and the PD cassette of the PD system of FIG. 1, in accordance with some embodiments

FIG. 2 is a perspective view of the PD machine 102 and the PD cassette 112 of the PD system 100 of FIG. 1, in accordance with some embodiments. As depicted in FIG. 2, the PD cassette 112 is placed proximate the cassette interface 110. The cassette 112 contains pump chambers 138A, 138B, pressure sensing chambers 163A, 163B, and valve chambers for controlling the flow of fluid through the cavities of the cassette 112. The cassette 112 is connected to the dialysate bag lines 126, the heater bag line 128, the patient line 130, and the drain line 132.

The cassette interface 110 includes a surface having holes formed therein. The PD machine 102 includes pistons 133A, 133B with piston heads 134A, 134B attached to piston shafts. The piston shafts can be actuated to move the piston heads 133A, 133B axially within piston access ports 136A, 136B formed in the cassette interface 110. The pistons 133A, 133B are sometimes referred to herein as pumps. In some embodiments, the piston shafts can be connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward on the lead screws. The stepper motors can be controlled by driver modules. The nuts, in turn, are connected to the piston shafts, which cause the piston heads 134A, 134B to move axially inward and outward as the stepper motors drive the lead screws. Stepper motor controllers provide the necessary current to be driven through the windings of the stepper motors to move the pistons 133A, 133B. The polarity of the current determines whether the pistons 133A, 133B are advanced or retracted. In some embodiments, the stepper motors require 200 steps to make a full rotation, and this corresponds to 0.048 inches of linear travel of the piston heads 134A, 134B.

In some embodiments, the PD system 100 also includes encoders (e.g., optical quadrature encoders) that measure the rotational movement and direction of the lead screws. The axial positions of the pistons 133A, 133B can be determined based on the rotational movement of the lead screws, as indicated by feedback signals from the encoders. Thus, measurements of the position calculated based on the feedback signals can be used to track the position of the piston heads 134A, 134B of the pistons 133A, 133B.

When the cassette 112 is positioned within the cassette compartment 114 of the PD machine 102 with the door 108 closed, the piston heads 134A, 134B of the PD machine 102 align with the pump chambers 138A, 138B of the cassette 112 such that the piston heads 134A, 134B can be mechanically connected to dome-shaped fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B. Retraction of the piston heads 134A, 134B away from the cassette 112 can increase the volume of the pump chambers 138A, 138B and cause dialysate to be drawn into the pump chambers 138A, 138B.

The cassette 112 also includes pressure sensor chambers 163A, 163B. When the cassette 112 is positioned within the cassette compartment 114 of the PD machine 102 with the door 108 closed, pressure sensors 151A, 151B align with the pressure sensor chambers 163A, 163B. Portions of a membrane that overlies the pressure sensor chambers 163A, 163B adhere to the pressure sensors 151A, 151B using vacuum pressure. Specifically, clearance around the pressure sensors 151A, 151B communicates vacuum to the portions of the cassette membrane overlying the pressure sensing chambers 163A, 163B to hold those portions of the cassette membrane tightly against the pressure sensors 151A, 151B. The pressure of fluid within the pressure sensing chambers 163A, 163B causes the portions of the cassette membrane overlying the pressure sensor chambers 163A, 163B to contact and apply a force to the pressure sensors 151A, 151B.

The pressure sensors 151A, 151B can be any sensors that are capable of measuring the fluid pressure in the pressure sensor chambers 163A, 163B. In some embodiments, the pressure sensors are solid state silicon diaphragm infusion pump force/pressure transducers. One example of such a sensor is the model 1865 force/pressure transducer manufactured by Sensym® Foxboro ICT. In some embodiments, the force/pressure transducer is modified to provide increased voltage output. The force/pressure transducer can, for example, be modified to produce an output signal of 0 to 5 volts.

Figure 3:
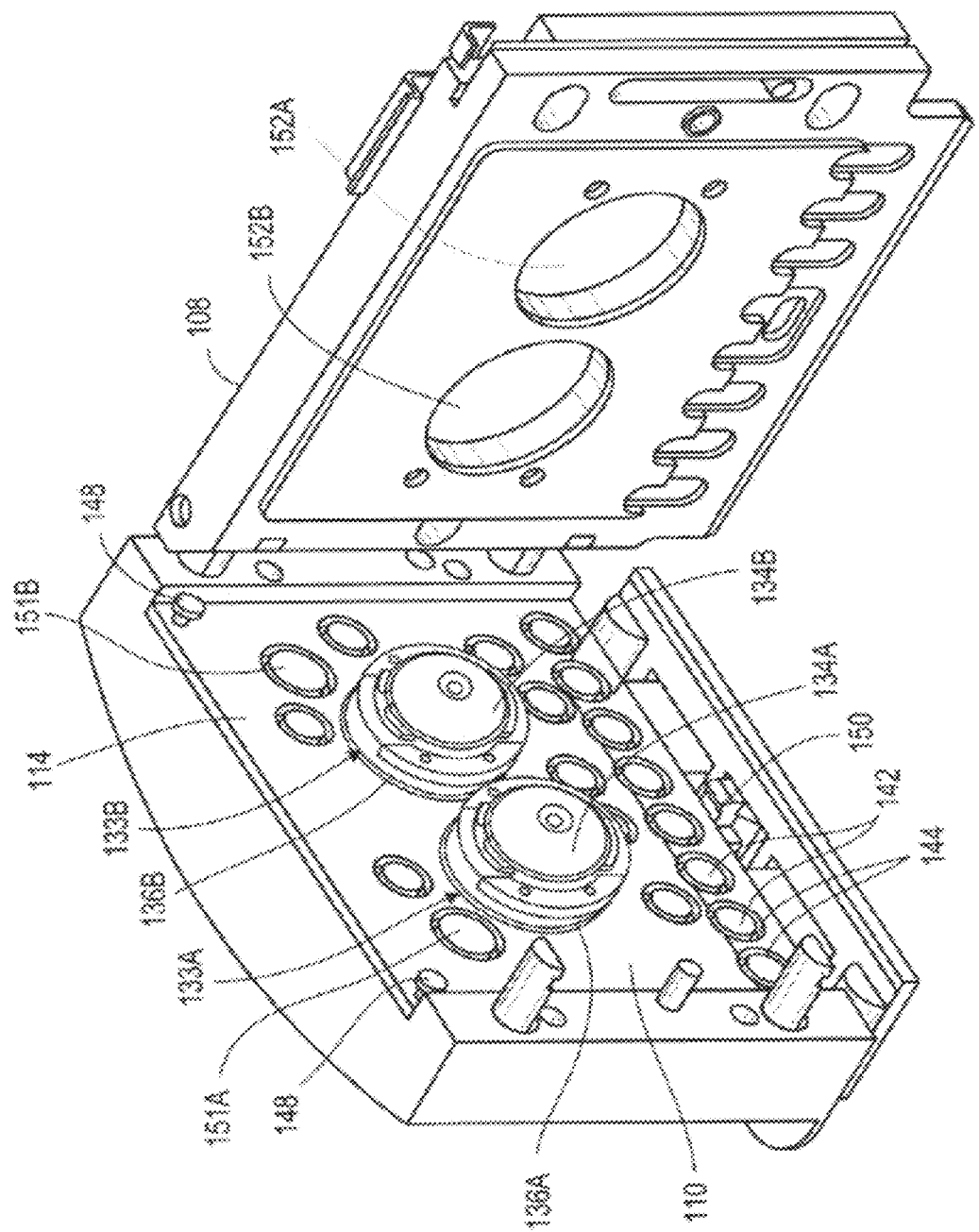
FIG. 3 is a perspective view of an open cassette compartment of the PD machine of FIG. 1, in accordance with some embodiments.

FIG. 3 is a perspective view of an open cassette compartment 114 of the PD machine 102 of FIG. 1, in accordance with some embodiments. As discussed above, the PD machine 102 includes pistons 133A, 133B disposed in piston access ports 136A, 136B, respectively. The PD machine 102 also includes multiple inflatable members 142 positioned within inflatable member ports 144 in the cassette interface 110. The inflatable members 142 align with depressible dome regions of the cassette 112 when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions of the cassette 112. The inflatable members 142 act, in cooperation with the depressible dome regions, as valves to direct dialysate through the cassette 112 in a desired manner during use. In particular, the inflatable members 142 bulge outward beyond the surface of the cassette interface 110 and into contact with the depressible dome regions of the cassette 112 when inflated, and retract into the inflatable member ports 144 and out of contact with the cassette 112 when deflated. By inflating certain inflatable members 142 to depress their associated dome regions on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

In some embodiments, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD machine 102 defines cylindrical recesses 152A, 152B that substantially align with the pistons 133A, 133B when the door 108 is in the closed position. When the cassette 112 is positioned within the cassette compartment 114 with the door 108 closed, the pump chambers 138A, 138B at least partially fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the surface of the pump chambers 138A, 138B, and the other portions of the door 108 support the other regions or surfaces of the cassette 112. The door 108 can counteract the forces applied by the inflatable members 142 and, therefore, allows the inflatable members 142 to actuate the depressible dome regions on the cassette 112. The engagement between the door 108 and the cassette 112 can also help to hold the cassette 112 in a desired position within the cassette compartment 114 to further ensure that the pistons 133A, 133B align with the fluid pump chambers 138A, 138B of the cassette 112.

The control unit 139 of FIG. 1 is connected to the pressure sensors 151A, 151B, to the stepper motors (e.g., the drivers for the stepper motors) that drive the pistons 133A, 133B, and to the encoders that monitor rotation of the lead screws attached to the stepper motors such that the control unit 139 can receive signals from and transmit signals to those components of the PD system 100. The control unit 139 monitors the components to which it is connected to determine whether any complications exist within the PD system 100, such as the presence of an occlusion or blockage in the patient line 130.

Figure 4:
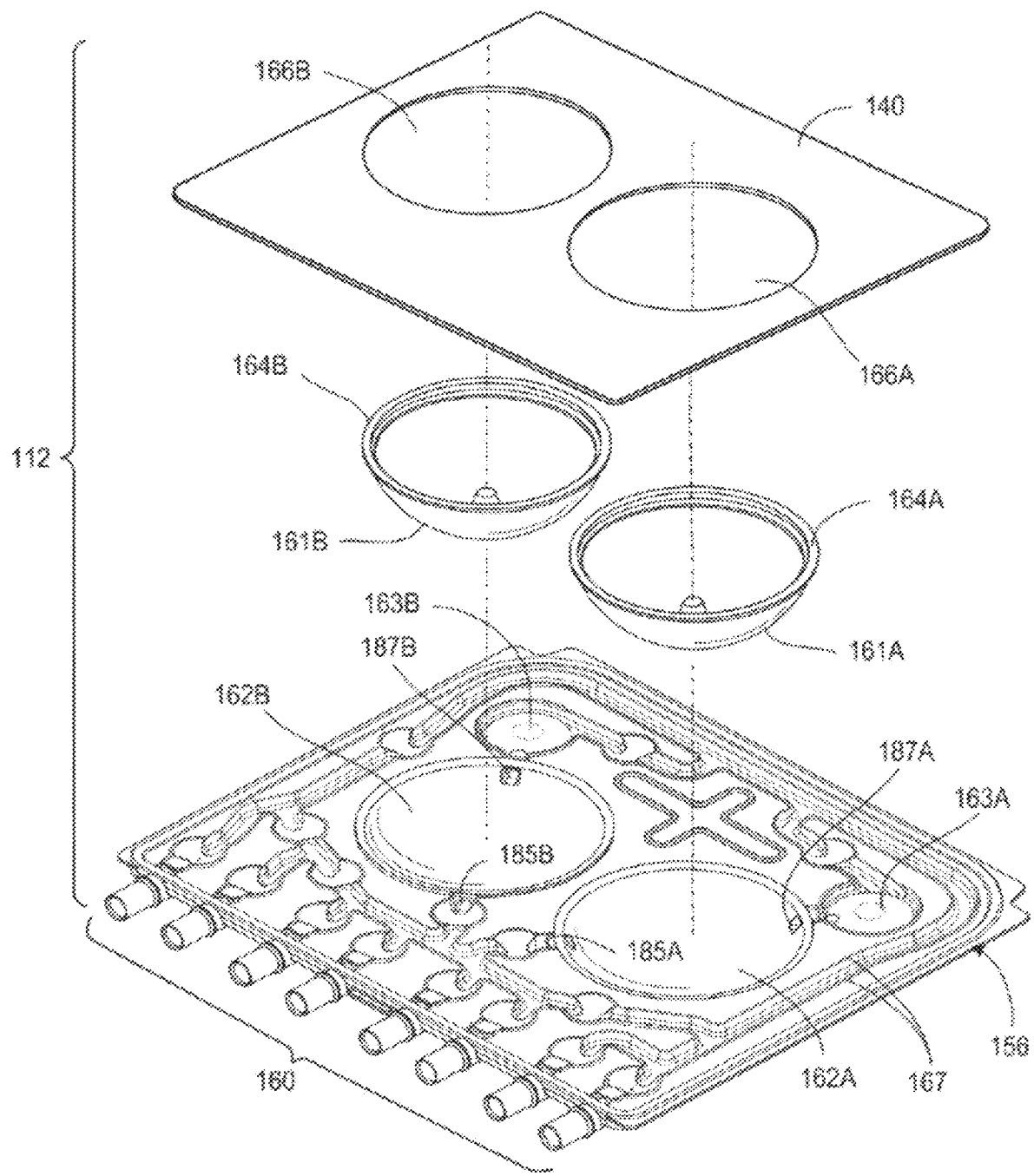
FIG. 4 is an exploded, perspective view of the PD cassette of FIG. 2, in accordance with some embodiments.
Figure 5:
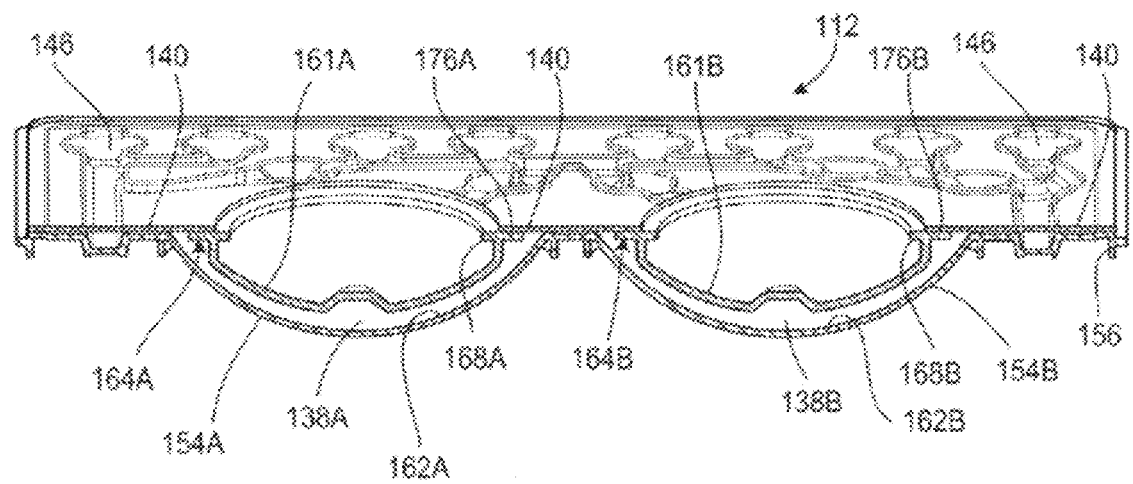
FIG. 5 is a cross-sectional view of the fully assembled PD cassette of FIG. 2, in accordance with some embodiments.
Figure 6:
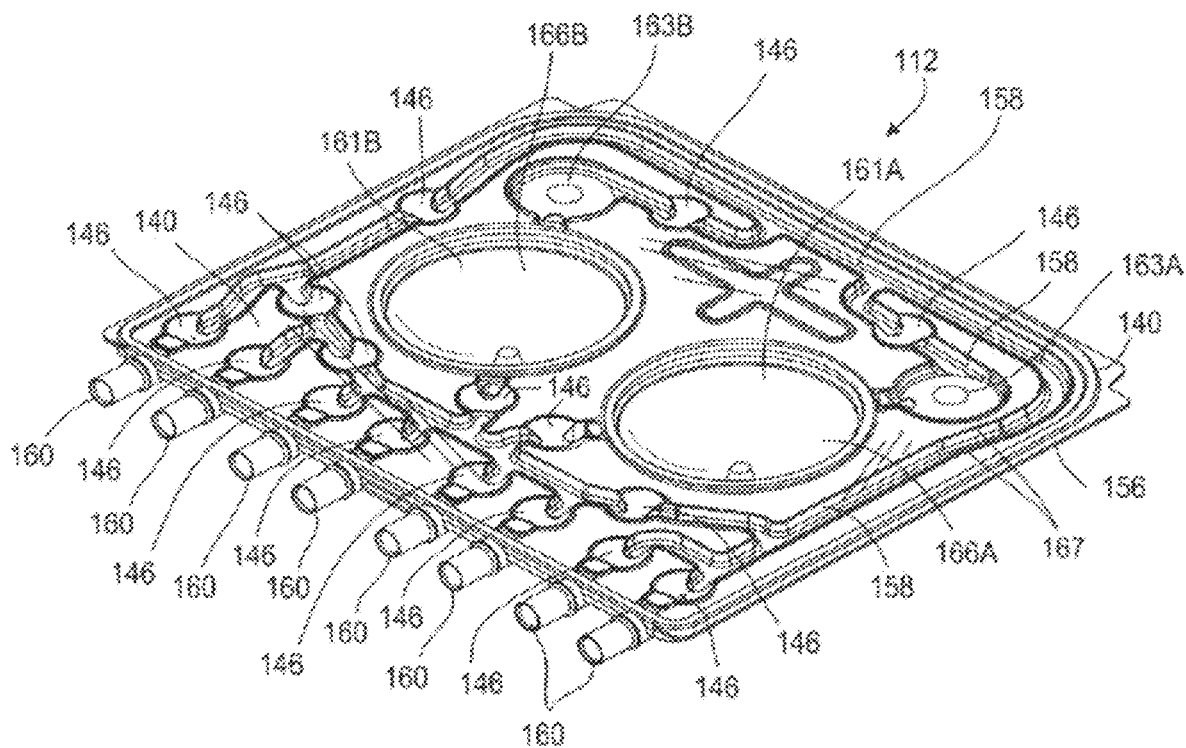
FIGS. 6 and 7 are perspective views of the PD cassette of FIG. 2 from a front side and a back side, respectively, in accordance with some embodiments.
Figure 7:
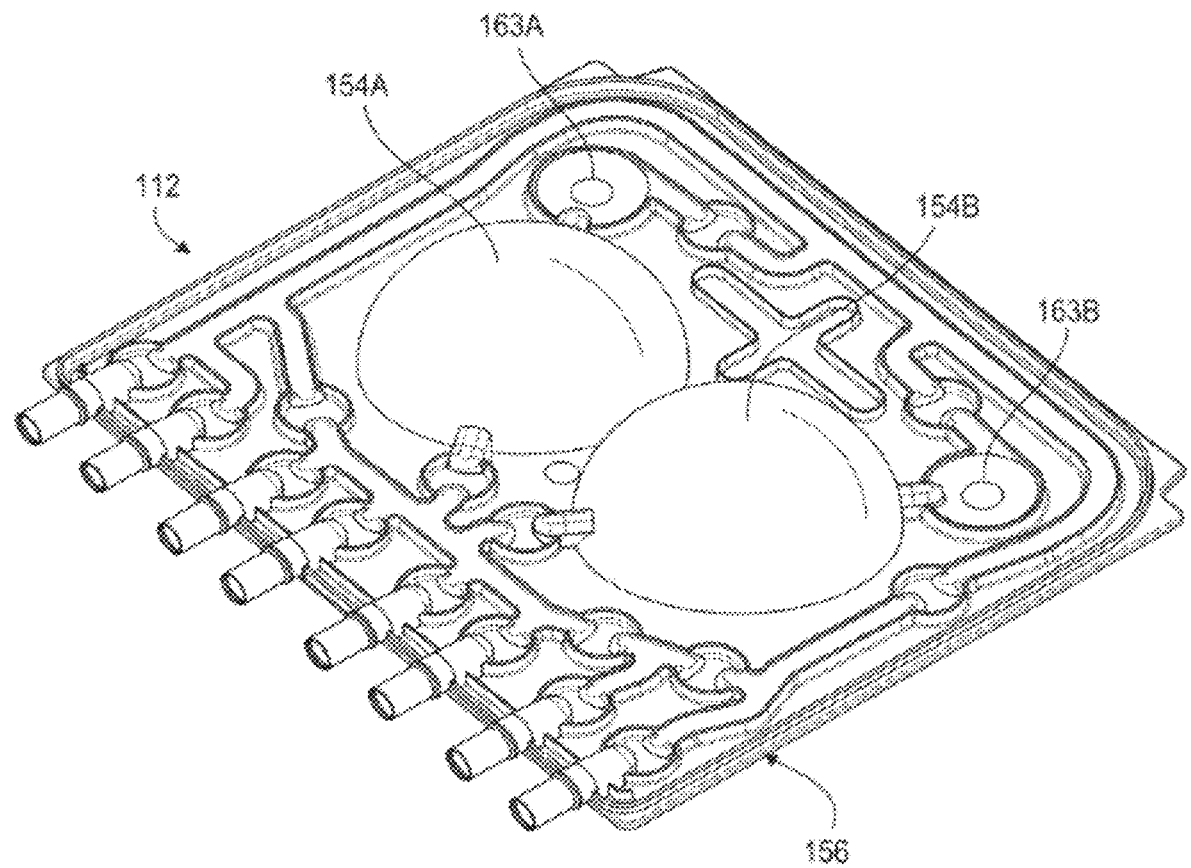

FIG. 4 is an exploded, perspective view of the PD cassette 112 of FIG. 2, in accordance with some embodiments. FIG. 5 is a cross-sectional view of the fully assembled PD cassette 112 of FIG. 2, in accordance with some embodiments. FIGS. 6 and 7 are perspective views of the PD cassette 112 of FIG. 2 from a front side and a back side, respectively, in accordance with some embodiments.

As depicted in FIGS. 4-7, the PD cassette 112 includes a flexible membrane 140 that is attached to a periphery of a tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102. In some embodiments, the dome-shaped fastening members 161A, 161B have a diameter, measured from the outer edges of annular flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B form annular projections 168A, 168B that extend radially inward and annular projections 176A, 176B that extend radially outward from the side walls of the dome-shaped fastening members 161A, 161B. When the piston heads 134A, 134B are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 1334B. Because the membrane 140 is attached to the dome-shaped fastening members 161A, 161B, movement of the dome-shaped fastening members 161A, 161B into and out of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable members 142 of the PD machine 102 act on the cassette 112 during use. The dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of the dialysate through the cassette 112 can be controlled through the selective depression of the depressible dome regions 146 by selectively inflating the inflatable members 142 of the PD machine 102.

The fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette 112, as depicted in FIGS. 1 & 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B or to allow fluid to flow from any of ports 185A, 185B, 187A, and 187B of the pump chambers 138A, 138B to any of the lines 126, 128, 130, and 132.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some embodiments, these components of the cassette 112 are formed of one or more polymers, such as polypropylene, polyvinyl chloride, polycarbonate, polysulfone, and other medical grade plastic materials. In some embodiments, these components can be formed of one or more metals or alloys, such as stainless steel. These components can alternatively be formed of various different combinations of the above-noted polymers and/or metals/alloys. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some embodiments, the membrane 140 is about 0.100 micron to about 0.150 micron in thickness. However, various other thicknesses may be sufficient depending on the type of material used to form the membrane 140. Any of various different materials that permit the membrane 140 to deflect in response to movement of the inflatable members 142 without tearing can be used to form the membrane 140. In some embodiments, the membrane 140 includes a three-layer laminate. In some embodiments, inner and outer layers of the laminate are formed of a compound that is made up of 60 percent Septon® 8004 thermoplastic rubber (i.e., hydrogenated styenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octane copolymer), and 35 percent Septon® 8004 thermoplastic rubber (i.e., hydrogenated styrenic block copolymer). The membrane 140 can alternatively include more or fewer layers and/or can be formed of different materials.

Figure 8:
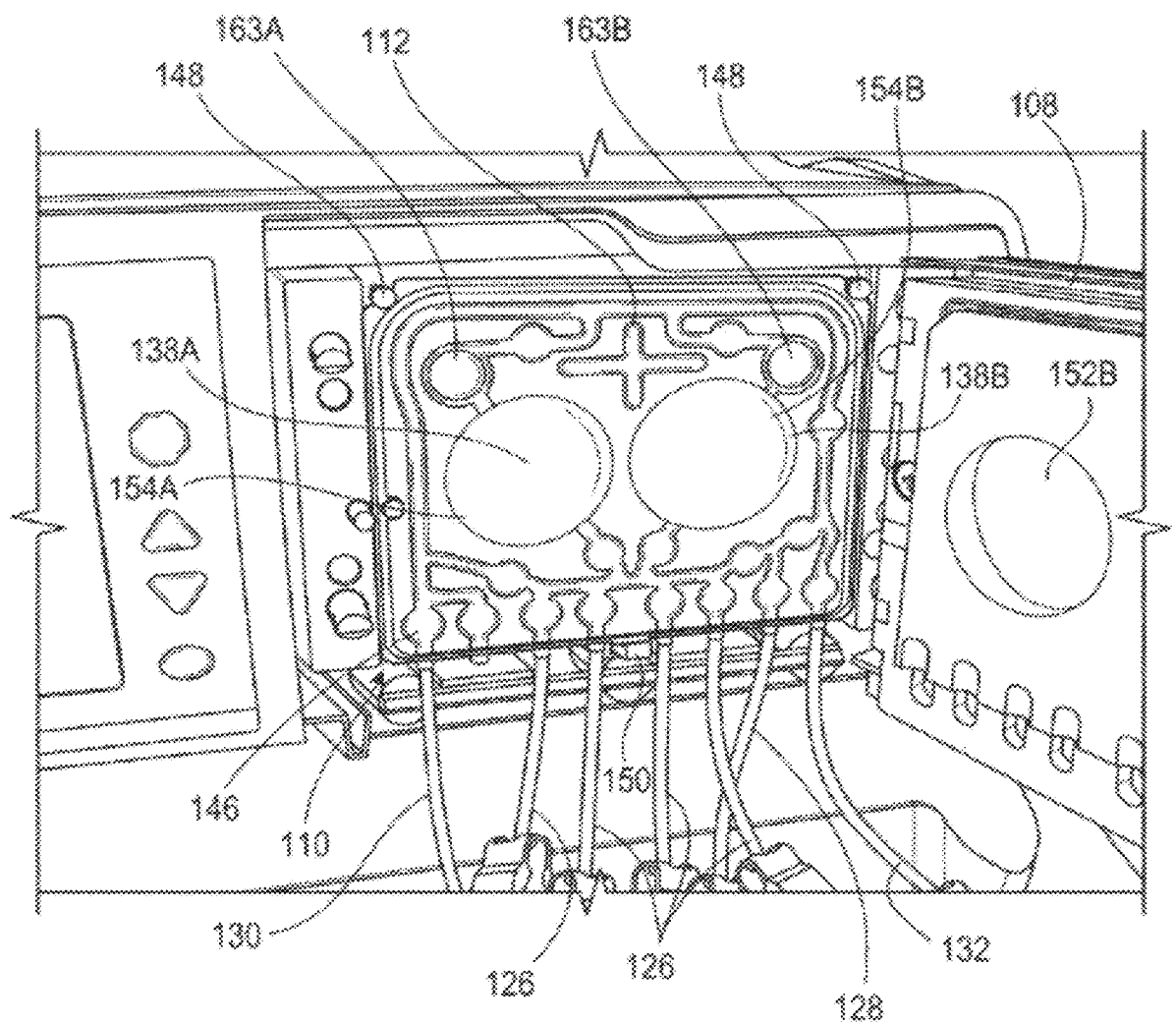
FIG. 8 illustrates the PD cassette seated against the cassette interface, in accordance with some embodiments.

FIG. 8 illustrates the PD cassette 112 seated against the cassette interface 110, in accordance with some embodiments. As depicted in FIG. 8, before starting a PD treatment, the door 108 of the PD machine 102 is opened to expose the cassette interface 110, and the cassette 112 is positioned with the dome-shaped fastening members 161A, 161B aligned with the pistons 133A, 133B of the PD machine 102, the pressure sensing chambers 163A, 163B aligned with the pressure sensors 151A, 151B of the PD machine 102, the depressible dome regions 146 aligned with the inflatable members 142 of the PD machine 102, and the membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette 112 act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward towards the door 108. The pistons 133A, 133B are typically retracted into the piston access ports 136A, 136B during installation of the cassette 112 to avoid interference between pistons 133A, 133B and the dome-shaped fastening members 161A, 161B and, therefore, increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. The compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146. The patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to the dome-shaped fastening members 161A, 161B of the cassette 112 to permit priming of the cassette 112 and one or more of the lines 126, 128, 130, and 132. Once these components have been primed, the PD treatment can be initiated.

Figure 9:
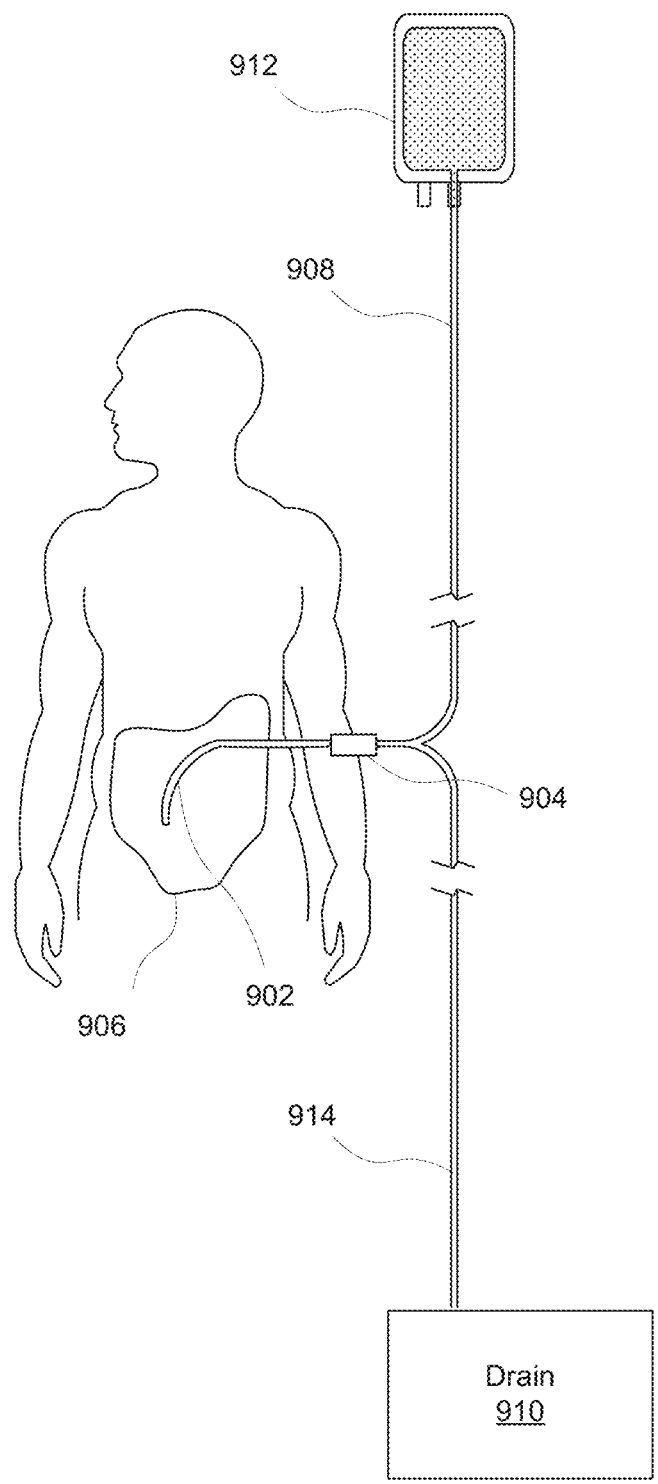
FIG. 9 is a conceptual illustration of a PD treatment that does not utilize a PD cycler, in accordance with prior art.

FIG. 9 is a conceptual illustration of a PD treatment that does not utilize a PD cycler, in accordance with prior art. Traditionally, a PD treatment could be performed using gravity to assist with filling and draining the patient's abdominal cavity. A dialysate bag 912 is hung above the patient and connected to a patient line 908. The patient line 908 is connected to port 904 that is connected to the surgically implanted catheter 902. The dialysate flows into the abdominal cavity 906 during a fill phase and waste is transferred across the peritoneum into the dialysate.

Then, during a drain phase, the effluent is allowed to drain through a drain line 914 into a drain 910. The drain 910 can be a receptacle such as an empty bag or canister. Alternatively, the drain 910 can be an open receptacle, such as a sink or toilet connected to the building's plumbing system.

Although not explicitly shown, the connection at the port 904 can include a valve that enables the patient or a caretaker to block the drain line 914 during the fill phase such that clean dialysate is not simply shunted directly to the drain 910.

In some circumstances, this PD treatment is not as effective as automated PD machines because the pressure in the patient line 908 is limited by the length of the line and the height at which the bag can be hung relative to the patient. Blockages in the catheter 902 can prevent dialysate from filling the abdominal cavity 906. These issues can be alleviated by utilizing a PD machine, such as the one detailed above. However, the PD machine can cause issues during the drain phase of the PD cycle. For example, negative pressure in the drain line 914 caused by the pump can cause the line to collapse, thereby preventing effluent from being removed from the abdominal cavity. The negative pressure can also cause tissue in the abdominal cavity to be suctioned up against the orifices in the catheter, which can also prevent fluid from entering the drain line 914. These issues can be alleviated by a hybrid automated PD cycler that uses a pump during a fill phase of the PD cycle and bypasses the pump during a drain phase of the PD cycle.

Figure 10:
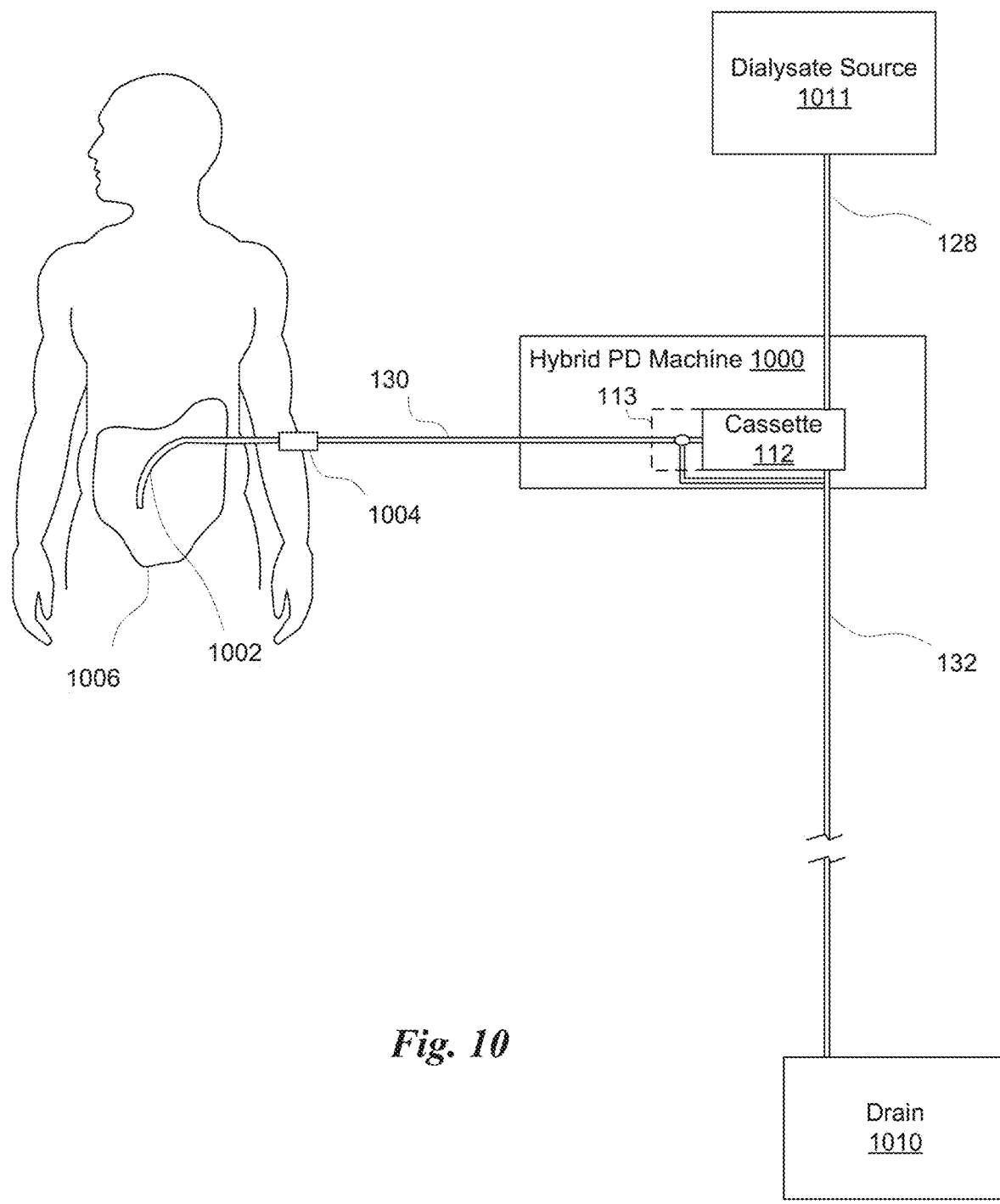
FIG. 10 illustrates a hybrid PD machine connected to a patient receiving a PD treatment, in accordance with some embodiments.

FIG. 10 illustrates a hybrid PD machine 1000 connected to a patient receiving a PD treatment, in accordance with some embodiments. The hybrid PD machine 1000 may be similar to the PD machine 102, and, as shown, the hybrid PD machine 1000 can be configured to disengage the pump or pumping action and/or bypass the pump during a drain phase of the PD cycle. More importantly, the hybrid PD machine 1000 provides a method of configuring the cassette 112 to use the pumping mechanism during a drain phase of the PD cycle or use a gravity-drain mechanism by bypassing the pumping mechanism during the drain phase, as manually or automatically configured. In some embodiments, the patient or caretaker can manually configure the hybrid PD machine 1000 to utilize or bypass the pumping mechanism during the drain phase of the PD cycle. In other embodiments, the hybrid PD machine 1000 can be initially configured to use the pump mechanism during a PD cycle. During the PD cycle, the drain phase can be monitored to detect an alarm related to improper drainage (e.g., occlusion of the patient line or drain line, low drain volume, low flow rate, etc.). In response to the detected alarm, the hybrid PD machine 1000 can be automatically reconfigured to bypass the pumping mechanism during the drain phase of the current or next subsequent PD cycle.

As depicted in FIG. 10, a proximal end of the patient line 130 is connected to a cassette 112 that is installed in the hybrid PD machine 1000. A distal end of the patient line 130 is connected to the patient's abdomen 1006 via a catheter 1002. The catheter 1002 is connected to the patient line via a port 1004. In some embodiments, the patient line 130 can be a hollow tube formed from distensible and/or flexible material that is at least partially distended by operating pressures in the hybrid PD machine 1000. In other words, fluid pressure causes the outer walls of the hollow tube to expand radially, thereby enabling the fluid to flow through the center of the tube. For example, in some embodiments, the patient line 130 can be made of an elastomeric material such as a polymer that expands in response to positive operating pressures in the fluid caused by the pumping action of the hybrid PD machine 1000. The patient line 130, the port 1004, and the catheter 1002 are sometimes referred to as the patient line-catheter conduit, or simply conduit.

It will be appreciated that, during the fill phase of the PD cycle, at least one of the pump chambers 138A, 138B and pressure sensing chambers 163A, 163B of the cassette 112 are fluidly coupled to the proximal end of the patient line 130 in order to induce fluid (e.g., dialysate solution) from a dialysate source 1011 to flow through the patient line 130 in response to movement of the pistons 133A, 133B. The pressure sensors 151A, 151B can continuously monitor the fluid pressure in the corresponding pressure sensing chambers 163A, 163B. The signal generated by the pressure sensors 151A, 151B is indicative of the magnitude and direction of the fluid flow into or out of the pump chambers 138A, 138B and, due to a particular configuration of the inflatable members 142, can be indicative of the fluid flow through the patient line 130, dialysate bag lines 126, or heater bag line 128 (connected to a heater bag 124).

As depicted in FIG. 10, a proximal end of the drain line 132 is connected to the cassette 112, and a distal end of the drain line 132 is connected to a drain 1010 or a drain receptacle such as a bag, tub, or other receptacle capable of holding fluid. In some embodiments, the drain line 132 can be a hollow tube formed from distensible and/or flexible material that is at least partially distended by operating pressures in the PD machine 102. In some embodiments, the drain line 132 can be made of an elastomeric material such as a polymer that expands in response to positive operating pressures in the fluid caused by the pumping action of the hybrid PD machine 1000. It will be appreciated that the distal end of the drain line 132 can be open to the air in order to promote fluid discharge into the drain 1010. In some embodiments, the drain line 132 can include a one-way valve, such as a check valve, that prevents backflow of fluid from the drain 1010 to the cassette 112. The one-way valve can also prevent air in the drain line from being introduced into the cassette 112, which can decrease the reliability of readings of the pressure sensors 151A, 151B.

During a drain phase of the PD cycle, the cassette is configured to allow the effluent (e.g., dialysate plus waste products) to bypass and/or otherwise disengage the pump or pumping action of the cassette 112, for example, by bypassing the chambers 138A, 138B. This is shown schematically in the figure by portion 113 of the cassette 112. In an embodiment, to perform the pump bypassing action, the inflatable members 142 can be configured such that the patient line 130 is directly shunted to the drain line 132. In other embodiments, one or more valves of the cassette 112 may be controlled to provide a bypass flow path for dialysate to drain to the drain 1010 without use of a pump or pumping action of the cassette 112. This allows the dialysate in the patient's abdomen to drain naturally similar to the conventional PD treatment without the use of the PD cycler. It will be appreciated that naturally draining of the dialysate from the patient's abdomen may occur as a result of gravity and/or the patient's abdomen may naturally force the fluid into the catheter 1002 due to the excess fluid that was pumped into the patient's abdomen during the fill phase and dwell phase of the PD cycle. The pressure in the fluid works to force the fluid into the patient line 130 and out the drain line 132. In addition, once the fluid begins to drain, as long as the drain 1010 is located below the patient's abdominal cavity, a siphon can be established that helps to drain most of the excess dialysate from the patient's abdominal cavity.

Figure 11A:
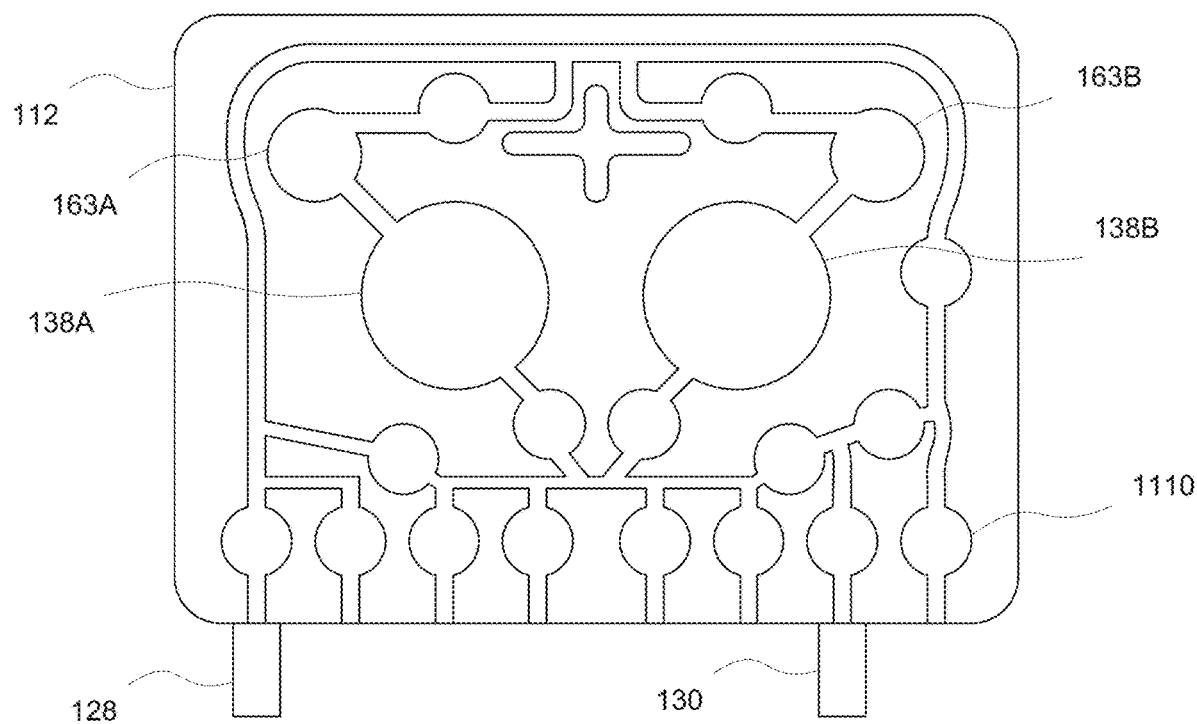
FIGS. 11A-11F illustrate the configuration of the cassette during a fill phase of the PD cycle, in accordance with some embodiments.

FIGS. 11A-11F illustrate the configuration of the cassette 112 during a fill phase of the PD cycle, in accordance with some embodiments. As depicted in FIG. 11A, the cassette 112 includes a number of cavities and fluid paths connecting the cavities. The cassette 112 includes two pump chambers 138A, 138B each connected to a corresponding pressure chamber 163A, 163B, respectively. A heater bag line 128 is connected to a first port on the cassette 112 and the patient line 130 is connected to a second port on the cassette 112. The cassette 112 includes a number of valves 1110 disposed in the fluid pathways that enable the PD machine 102 to direct the fluid within the cassette 112 by opening and closing valves 1110, using inflatable members 142, in a specific configuration and sequence.

Figure 11B:
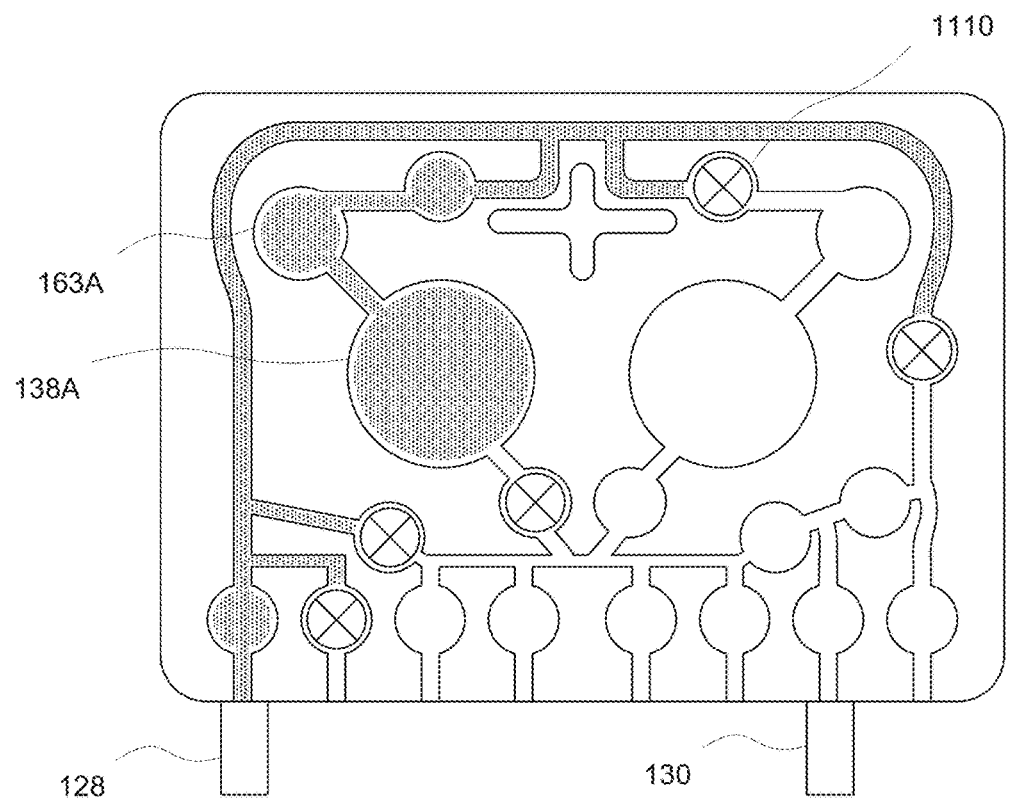

As depicted in FIG. 11B, to begin the patient fill phase, the inflatable members 142 are configured to create an open fluid flow path between the pump chamber 138A and the heater bag line 128, and then the piston 133A is retracted, to draw warm dialysate from the heater bag 124 to the pump chamber 138A. The warm dialysate travels from the heater bag 124 through the heater bag line 128 and into the pump chamber 138A. Closed valves are shown as a circle with an x inscribed therein.

Figure 11C:
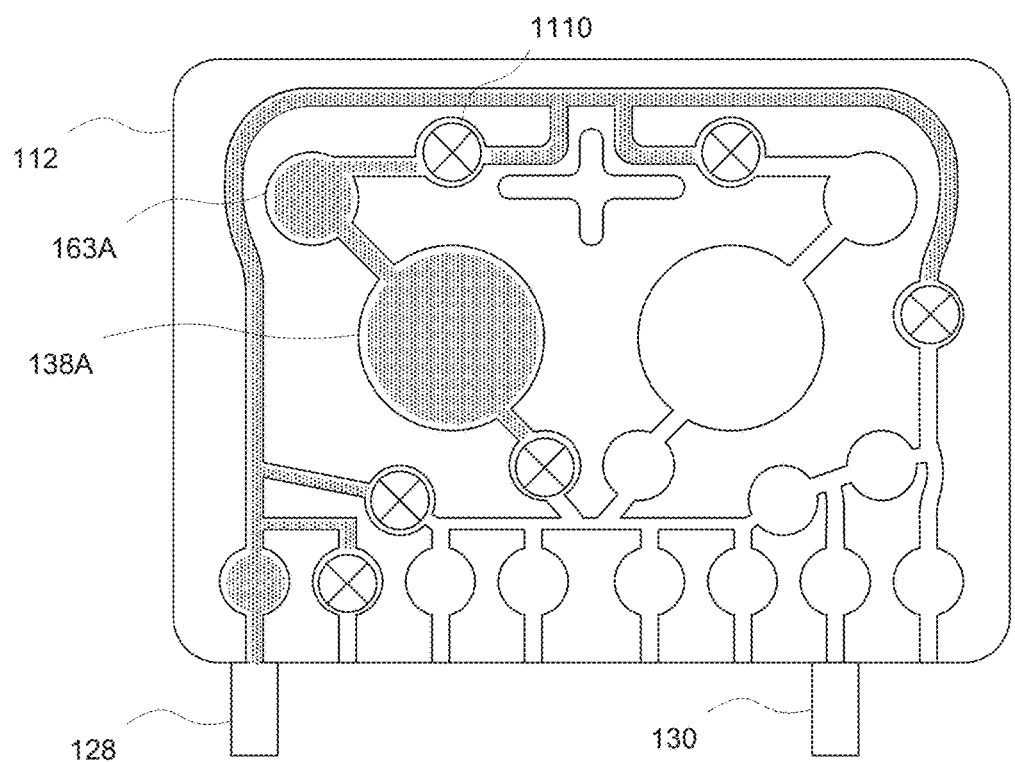

As depicted in FIG. 11C, an additional valve 1110 is closed, trapping fluid in the pump chamber 138A and pressure chamber 163A. The piston 133A can be cycled to measure the amount of fluid in the pump chamber 138A by monitoring a pressure transducer disposed against the pressure chamber 163A.

Figure 11D:
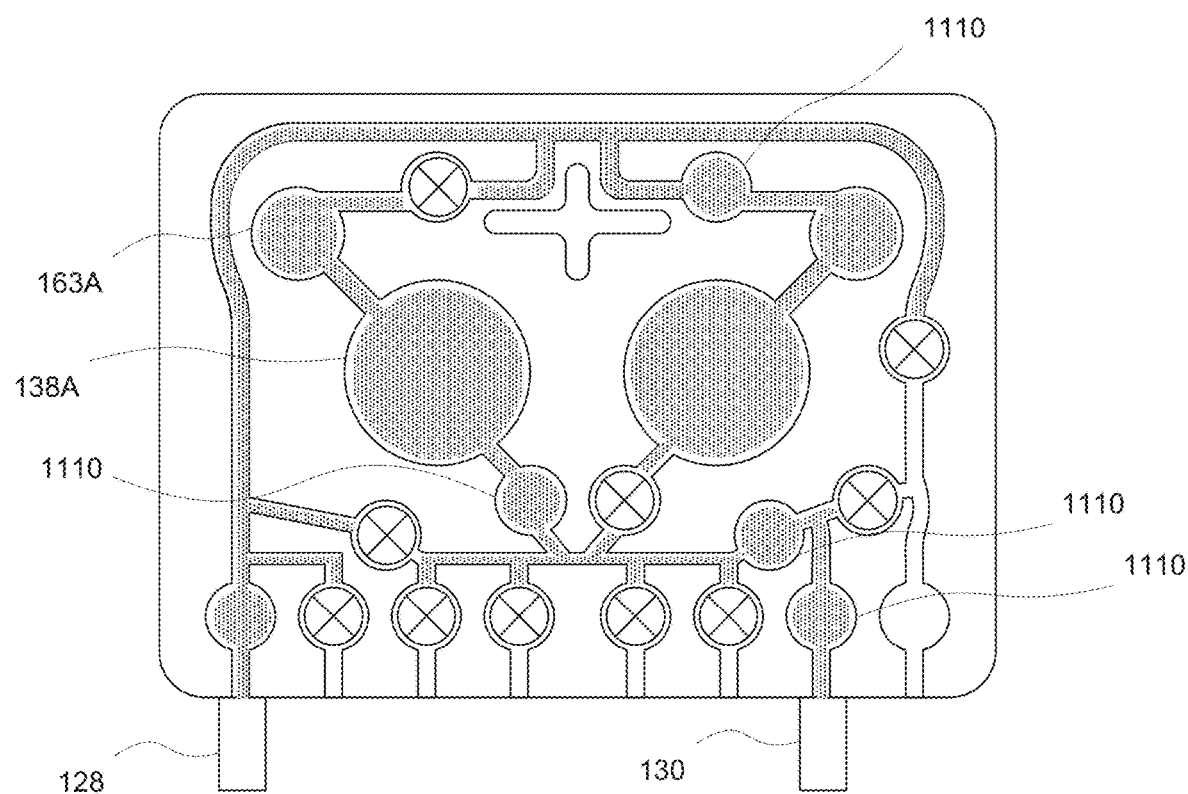

As depicted in FIG. 11D, the valves 1110 can then be configured to connect the pump chamber 138A to the patient line 130. The piston 133A is operated to force the fluid from the pump chamber 138A into the patient line 130. At the same time, the second pump chamber 138B can be fluidly coupled to the heater bag line 128 to draw dialysate into the second pump chamber 138B. It will be appreciated as the piston 133A is extending to force fluid out of pump chamber 138A, the piston 133B is retracting to draw fluid into the pump chamber 138B.

Figure 11E:
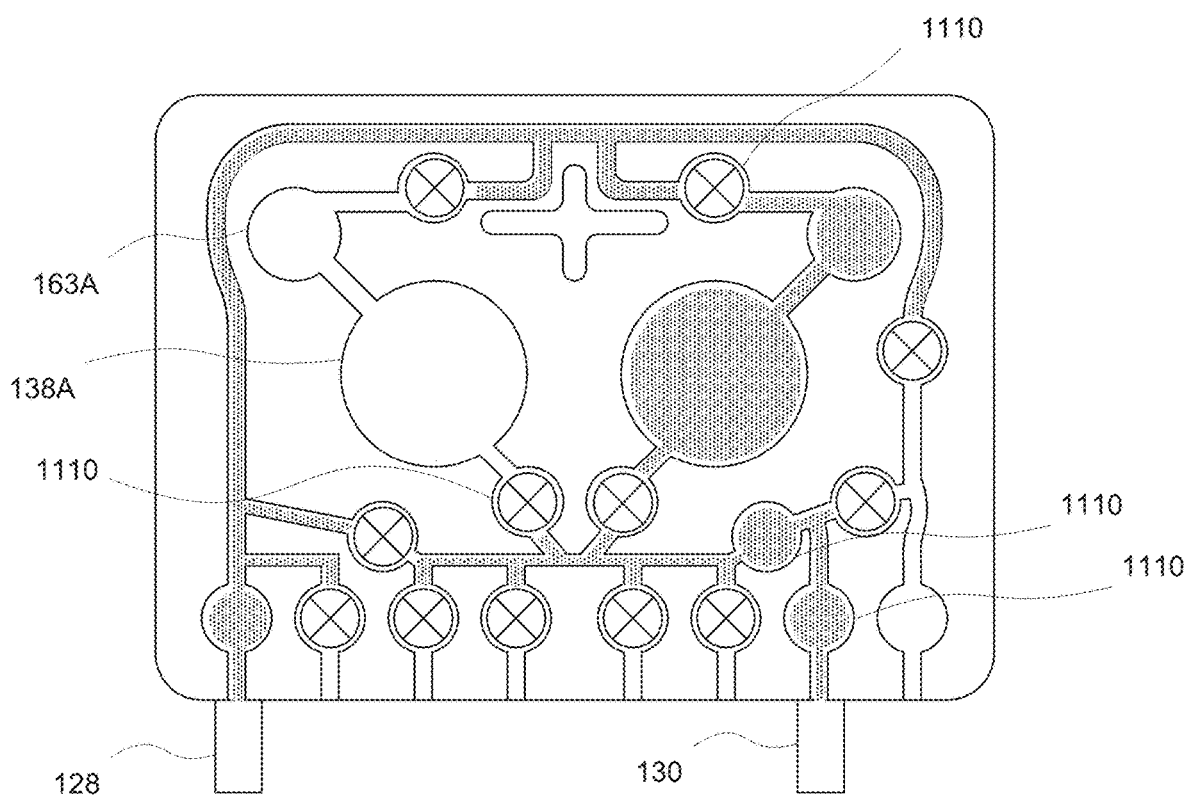

As depicted in FIG. 11E, the valves 1110 are configured to disconnect the patient line 130 from both pump chamber 138A and pump chamber 138B. The configuration of the valves 1110 traps fluid in the pump chamber 138B and pressure chamber 163B. The piston 133B can be cycled to measure the amount of fluid in the pump chamber 138B by monitoring a pressure transducer disposed against the pressure chamber 163B.

Figure 11F:
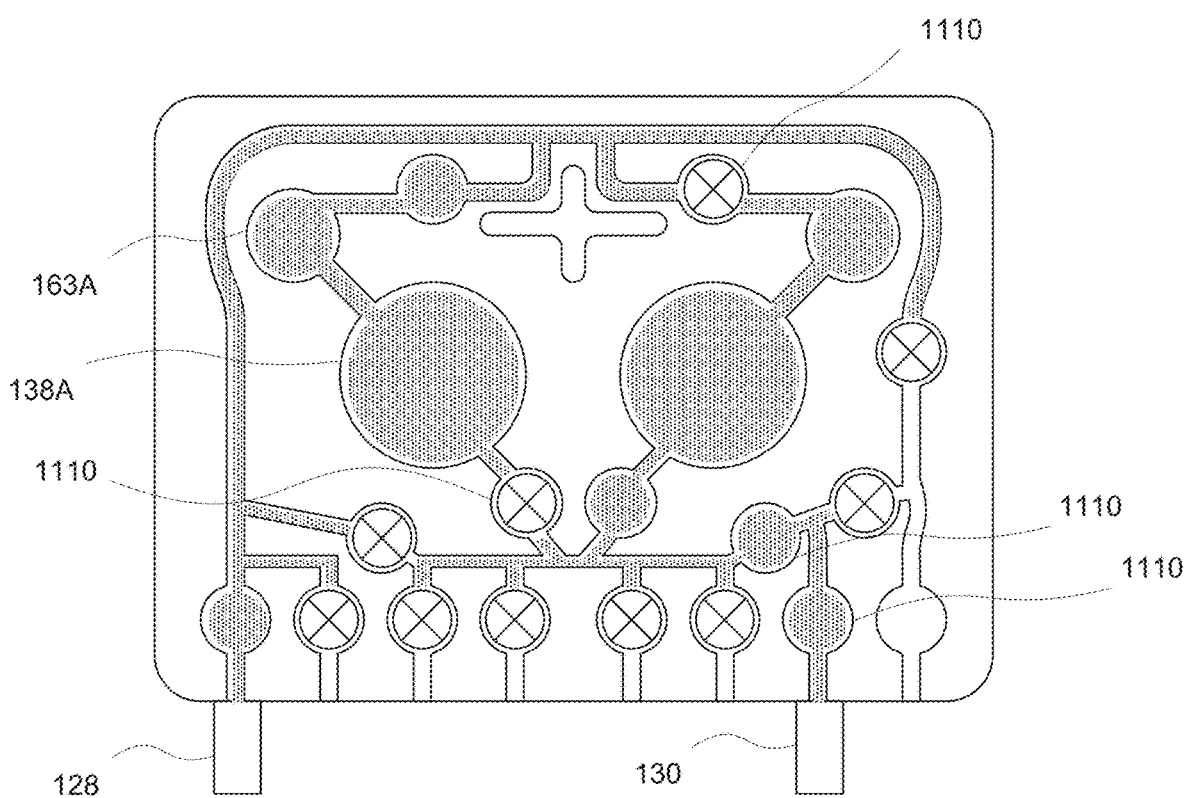

As depicted in FIG. 11F, the valves 1110 are then reconfigured to connect the pump chamber 138B to the patient line 130. The piston 133B extends to force fluid in the pump chamber 138B into the patient line 130. At the same time, the pump chamber 138A is connected to the heater bag line 128, and the piston 133A retracts to draw fluid into the pump chamber 138A. This cycle can be repeated a number of times until the total amount of fluid forced into the patient line 130 meets a desired amount of fluid as prescribed for that patient. Once the fill phase is complete, the valves 1110 can be configured to disconnect the patient line 130 from the rest of the cassette 112, thereby trapping fluid in the patient line 130 and/or the patient's abdomen. During the dwell phase, the dialysate is allowed to sit within the peritoneal cavity of the patient for a long period of time.

Figure 12A:
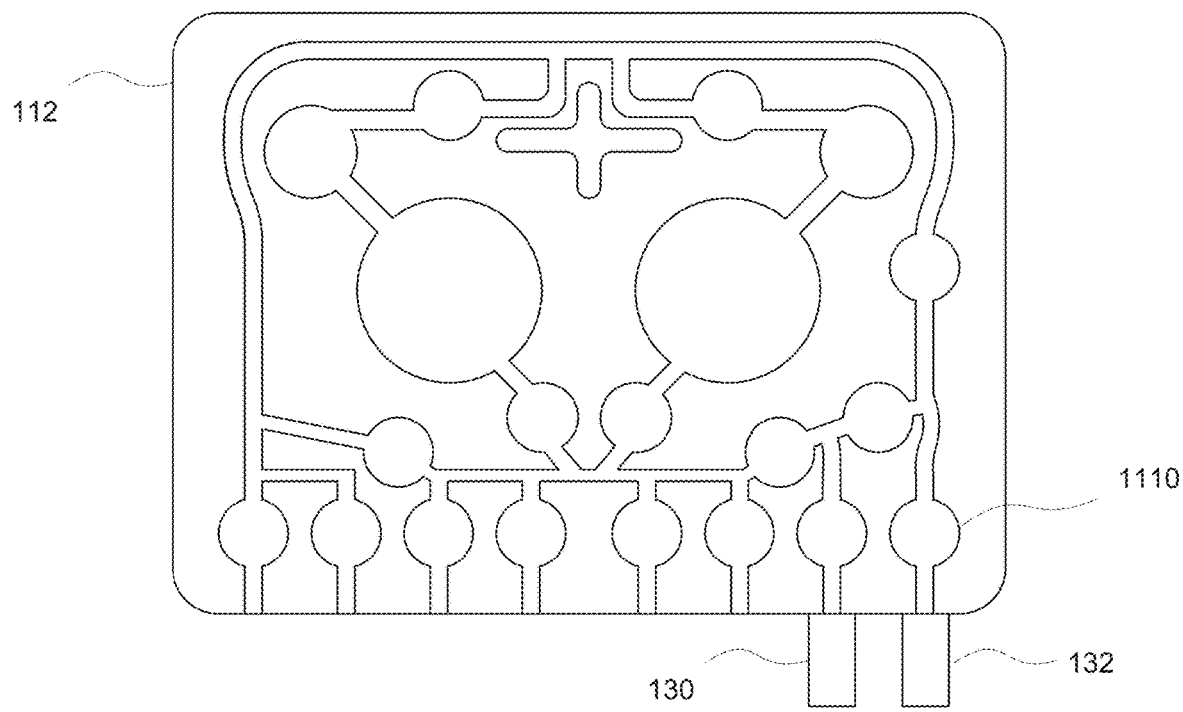
FIGS. 12A & 12B illustrate the configuration of the cassette during a drain phase of the PD cycle, in accordance with some embodiments.
Figure 12B:
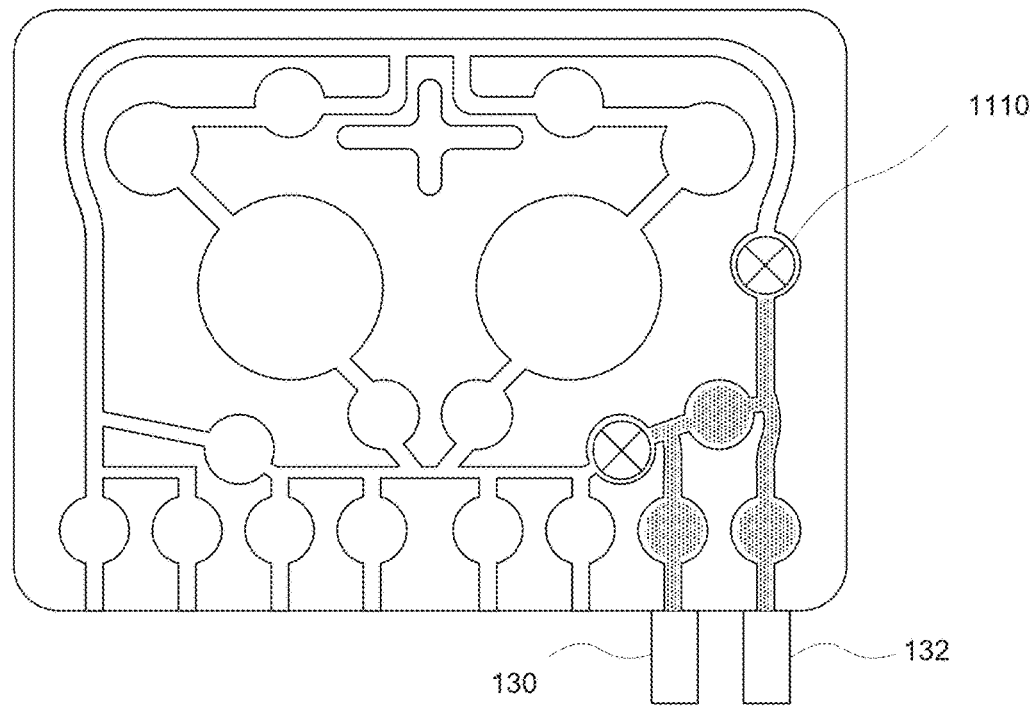

FIGS. 12A & 12B illustrate the configuration of the cassette 112 during a drain phase of the PD cycle, in accordance with some embodiments. As depicted in FIG. 12A, the cassette 112 is connected to the patient line 130 and a drain line 132. A number of valves 1110 can be configured to route fluid from the patient line 130 to the drain line 132.

As depicted in FIG. 12B, the valves 1110 are configured to allow fluid to flow directly from the patient line 130 to the drain line 132, bypassing the pump chambers 138A, 138B. Unlike conventional PD cyclers, the pump is not utilized to pump fluid from the patient's abdomen.

It will be appreciated that the hybrid automated PD cycler described above utilizes a cassette-type system that, during a fill phase, is configured to provide a fluid path with dialysate driven by action of the pump and, during a drain phase, is configured to bypass the pump by re-routing fluid within the cassette to use a different fluid path. However, in other embodiments, where, for example, the cassette 112 cannot be configured to bypass the pump, the cassette 112 can be modified from an original configuration to include a bypass circuit. This can include configuring the PD machine to include additional inflatable members to operate the bypass circuit in the modified cassette.

In yet other embodiments, a bypass circuit can be added to the fluid path external from the cassette 112. For example, instead of connecting the patient line 130 directly to the cassette 112, as shown in FIGS. 12A & 12B, the patient line 130 can be connected to a bypass valve. The bypass valve can then be connected to the cassette 112 where the patient line 130 was originally connected. The bypass valve can also be connected to the drain line 132. The bypass valve can then be operated to connect the cassette 112 to the patient line 130 during a fill phase of the PD cycle and to connect the patient line 130 to the drain line 132 during a drain phase of the PD cycle. In such embodiments, the effluent drained from the patient never re-enters the cassette 112 and is instead directly shunted to the drain line.

Figure 13A:
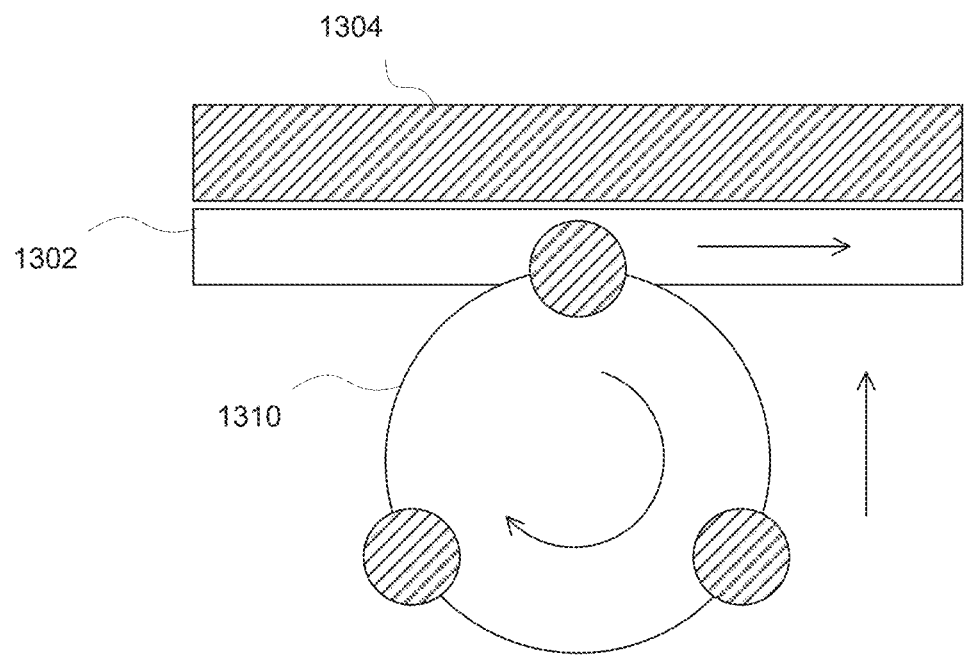
FIGS. 13A & 13B illustrate another type of pump that could be implemented in the hybrid automated PD machine, in accordance with some embodiments.
Figure 13B:
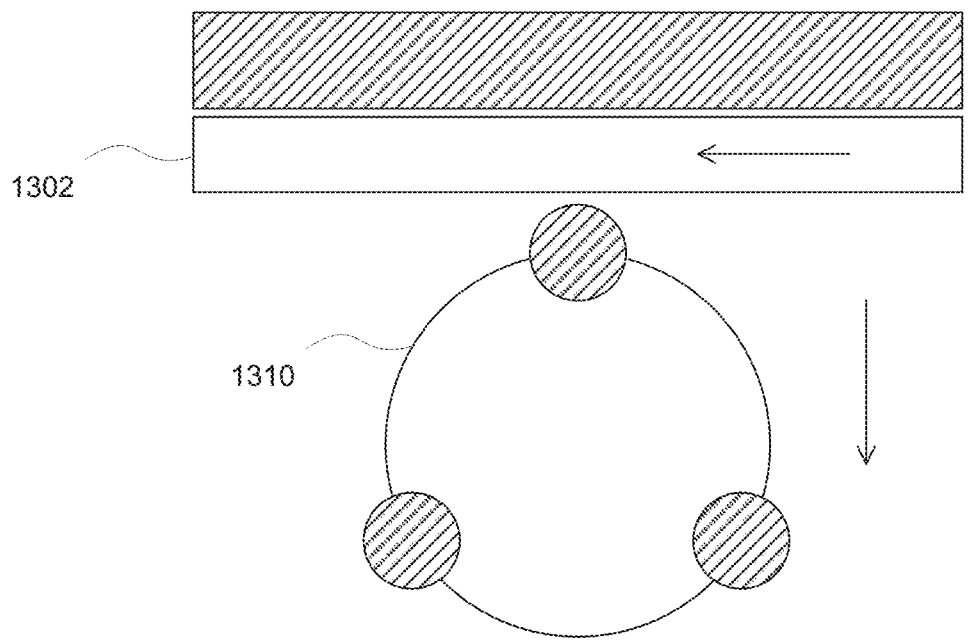

FIGS. 13A & 13B illustrate another type of pump that could be implemented in the hybrid automated PD machine, in accordance with some embodiments. Although the piston-type pump is used in certain PD machines, other PD machines can utilize a peristaltic pump. A peristaltic pump is a type of positive displacement pump that utilizes rollers that compress a flexible tube. The fluid in the tube is trapped between the rollers and forced to move in the tube in the direction of motion of the rollers.

As depicted in FIG. 13A, a motor is connected to a roller assembly 1310 and controls the roller assembly 1310 to rotate. A flexible tube 1302 is placed between the roller assembly and a fixed surface 1304. During rotation, the roller moves up into the flexible tube, thereby pinching or compressing the flexible tube. As the rotation continues, the roller moves from left to right or right to left relative to the surface 1304, and fluid in the flexible tube 1302 is forced in one direction depending on the direction of rotation of the roller assembly 1310. Direction of the flow can be reversed by reversing the direction of rotation of the roller assembly 1310.

It will be appreciated that although, in one embodiment, the roller assembly 1310 includes three rollers arranged at approximately 120 degrees apart around the circular housing of the roller assembly 1310, in other embodiments, the number or arrangement of rollers can be different and can include two rollers or four or more rollers. In addition, in some embodiments, the fixed surface 1304 can be curved such that the flexible tube follows a semi-circular path around the roller assembly 1310.

As depicted in FIG. 13B, the peristaltic pump can be disengaged in order to bypass the pump. By moving the roller assembly 1310 away from the fixed surface 1304, the rollers no longer compress the flexible tube 1302, thereby allowing fluid to flow freely from one end of the tube 1302 to the other end of the tube 1302.

It will be appreciated that the roller assembly 1310 is engaged, as shown in FIG. 13A, during a fill phase and a dwell phase of the PD cycle. Then, when the drain phase of the PD cycle is begun, the roller assembly 1310 is disengaged, allowing the fluid to flow freely through the flexible tube 1302.

In some embodiments, the PD system 1000 includes a peristaltic pump that can be engaged or disengaged as prescribed to complete the fill phase and the drain phase of the PD cycle. In other embodiments, the peristaltic pump is always engaged, but the flexible tube 1302 is connected to a bypass valve that can be opened in order to allow fluid to flow around the roller assembly 1310 and bypass the pumping mechanism. It will be appreciated that designing a bypass valve can enable conventional peristaltic pumps to be utilized in the PD system without modification.

One issue that is raised by bypassing the pumping mechanism is tracking the amount of fluid that is drained from a patient's abdominal cavity during the drain phase. Tracking the amount of fluid that is pumped into a patient and then drained from the patient is important when multiple PD cycles are performed automatically over the course of a night, for example. If drainage is obstructed, then the PD machine should not attempt to re-fill the patient's abdomen with additional fluid as this can cause complications for the patient. Conventional PD machines may track fluid flow by utilizing the pump. For example, the volume of the pump chamber 138A, 138B is known. After filling a pump chamber 138A, 138B, the PD machine can utilize a pressure transducer to check the amount of fluid that was in the pump chambers 138A, 138B and track how much fluid is being filled or drained from the patient. By bypassing the pump, the ability to track the fluid flow using this technique is not available. Therefore, an alternative technique for tracking the fluid flow can be desired to improve safety of the PD machine.

Figure 14A:
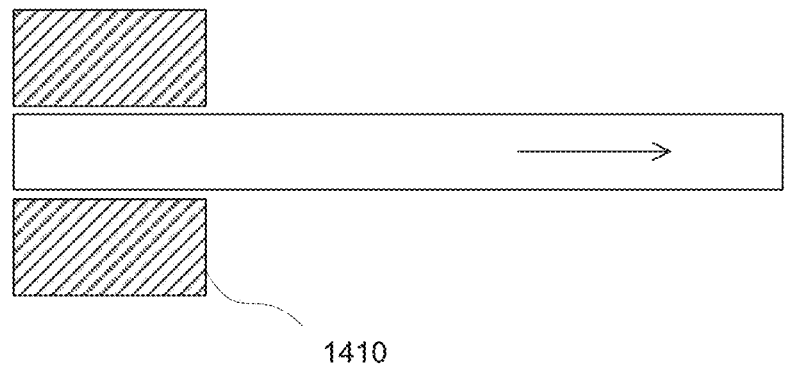
FIGS. 14A & 14B illustrate two techniques for monitoring the flow of fluid during a PD cycle, in accordance with some embodiments.
Figure 14B:
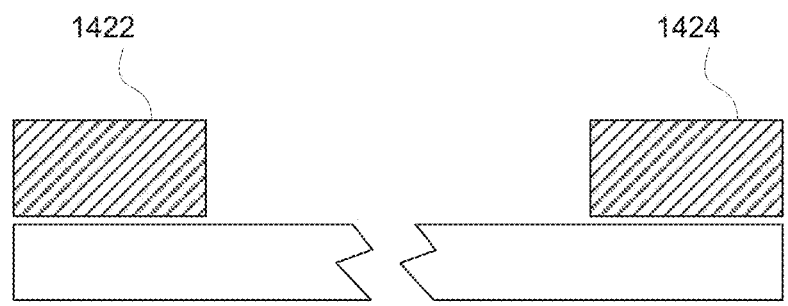

FIGS. 14A & 14B illustrate two techniques for monitoring the flow of fluid during a PD cycle, in accordance with some embodiments. As depicted in FIG. 14A, one technique for measuring flow rate inside a flexible tube utilizes an ultrasonic flow sensor 1410. Ultrasonic waves are transmitted into fluid flow opposite orientations and the difference in propagating velocity in the waves can be used to measure the flow of the fluid in the flexible tube. The ultrasonic flow sensor 1410 can be place on the patient line 130 or the drain line 132. By placing the ultrasonic flow sensor 1410 on the patient line 130, the ultrasonic flow sensor 1410 can be utilized to measure the fluid flow during both the fill phase and the drain phase of the PD cycle. An alert can be generated if the amount of fluid introduced to the patient line during the fill phase of the PD cycle is significantly different than the amount of fluid drained from the patient line during the drain phase of the PD cycle.

As depicted in FIG. 14B, another technique for measuring flow rate includes a pair of pressure transducers 1422, 1424. By placing the pressure transducers at different locations along a flexible tube, a differential in the fluid pressure along this known length of tube can be used to calculate the flow of fluid in the tube, where the cross-sectional area of the tube is known.

In other embodiments, other types of flow meters can be used to measure the fluid flow rate. For example, magnetic flow meters or tubine flow meters could be utilized in some embodiments.

Figure 15:
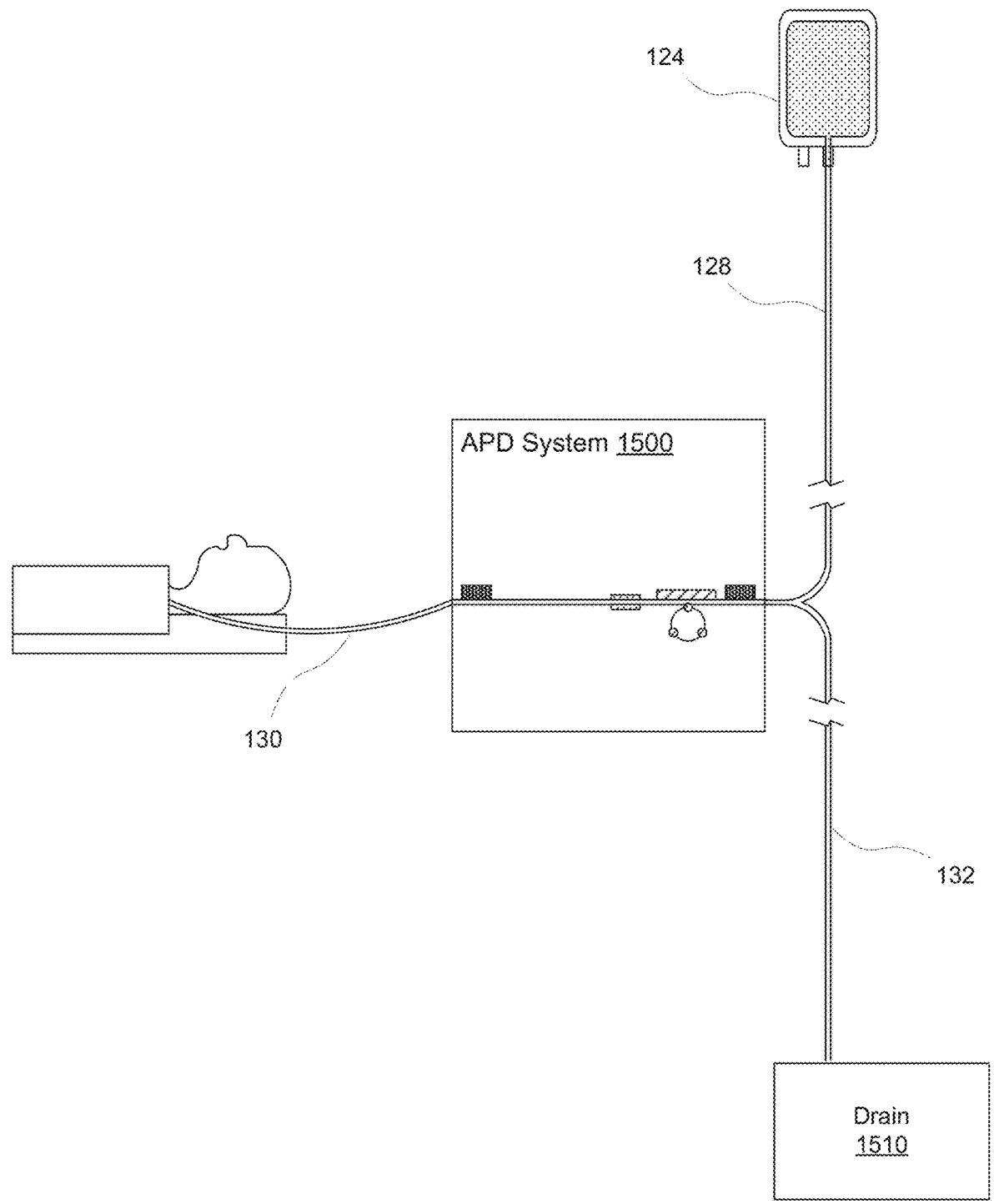
FIG. 15 illustrates a hybrid automated PD system, in accordance with some embodiments.

FIG. 15 illustrates a hybrid automated PD system 1500, in accordance with some embodiments. As depicted in FIG. 15, the hybrid APD system 1500 is connected to a heater bag 124 via a heater bag line 128. The heater bag line 128 supplies dialysate to a pump that is operated to cause dialysate to fill a patient's abdominal cavity via a patient line 130 during a fill phase of the PD cycle. Although the heater bag 124 and heater bag line 128 are schematically shown outside of the hybrid APD system 1500, in some embodiments, the heater bag 124 and heater bag line 128 may be part of an inline heating system located within the hybrid APD system 1500.

After the dialysate is allowed to dwell in the patient's abdomen, accumulating waste products across the peritoneum, the hybrid APD system 1500 enters a drain phase of the PD cycle. The pump is disengaged and fluid is allowed to drain naturally (e.g., as a result of gravity) to the drain 1510 via the drain line 132. The hybrid APD system 1500 includes one or more sensors used to monitor a fluid volume that drains from the patient during the drain phase of the PD cycle.

Figure 16:
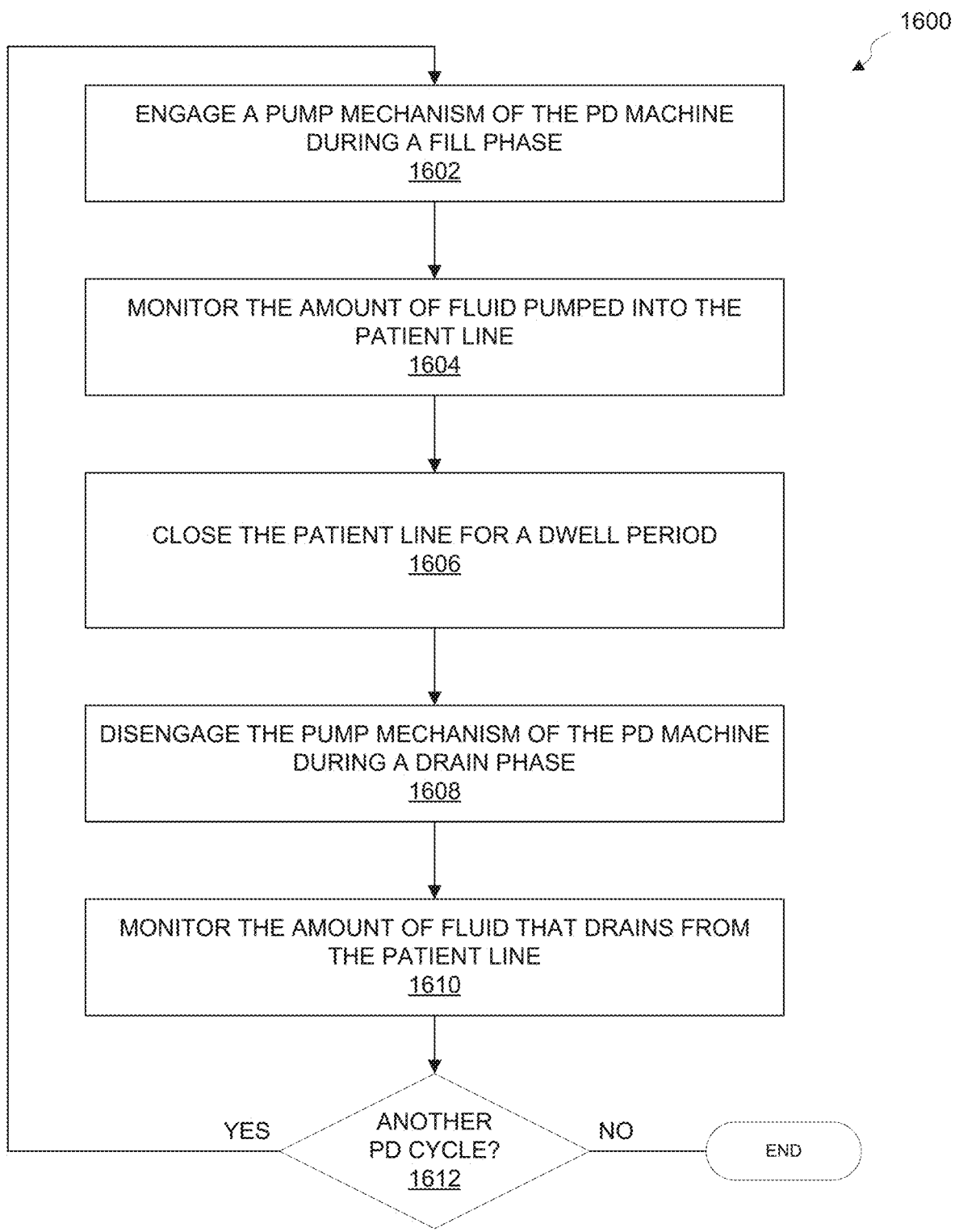
FIG. 16 is a flow diagram of method for conducting a PD treatment using a hybrid automated PD machine, in accordance with some embodiments.

FIG. 16 is a flow diagram of method 1600 for conducting a PD treatment using a hybrid automated PD machine, in accordance with some embodiments. It will be appreciated that the method 1600 is described as being performed by the PD machine 1000 or the hybrid automated PD machine 1500. More specifically, the various steps described below can be implemented by a processor, such as the control unit 139 of the PD machine 102, configured to execute a number of instructions. However, it will be appreciated that the method 1600 can be performed by any PD machine configured to drain fluid from a peritoneal cavity of a patient by bypassing the pump during a drain phase of a PD cycle. In various embodiments, the method 1600 can be implemented using hardware, software executed by a general purpose processor configured to control a specialized apparatus such as a PD machine, or a combination of hardware and software.

At step 1602, a pump of the PD machine is engaged during a fill phase of a PD cycle. In an embodiment, valves of a cassette 112 are configured to route fluid from a heater bag line 128 into one or more pump chambers of the cassette 112 before forcing the fluid from the one or more pump chambers into the patient line 130. In another embodiment, a roller assembly of a peristaltic pump is moved to engage the rollers with a flexible tube disposed between the roller assembly and a fixed surface. In some embodiments, a bypass valve may also be closed to prevent fluid from draining from the patient line 130 to the drain line 132.

At step 1604, an amount of fluid pumped into the patient line is monitored. In an embodiment, the fluid being drawn into and forced out of the pump chambers is monitored using the pistons and corresponding pressure transducers to measure an amount of fluid in the pump chamber that is forced into the patient line 130 during each cycle of the piston. In another embodiment, one or more sensors disposed between the pump and the patient line 130 are used to measure a flow of fluid into the patient line 130.

At step 1606, the patient line 130 is closed for a dwell phase of the PD cycle. The dwell phase is typically a number of minutes (e.g., 30 minutes, 60 minutes, etc.) during which the dialysate is allowed to remain in the patient's abdominal cavity to collect waste products. In an embodiment, a valve 1110 of the cassette proximate the patient line 130 port is closed to prevent fluid from flowing from the patient line 130 back into the cassette 112.

At step 1608, the pump of the PD machine is disengaged during a drain phase of the PD cycle. In an embodiment, the valves 1110 of the cassette are configured to create a fluid path in the cassette 112 from the patient line 130 to the drain line 132, where the fluid path does not flow through any of the pump chambers 138A, 138B of the cassette 112. In another embodiment, a bypass valve is opened to shunt the patient line 130 directly to the drain line 132. The bypass valve can be external to the cassette 112. In yet another embodiment, the roller assembly of a peristaltic pump is moved away from the fixed surface such that the roller assembly does not contact a flexible tube between the roller assembly and the fixed surface. In yet another embodiment, a bypass valve can be opened that allows fluid to bypass the roller assembly.

At step 1610, an amount of fluid that drains from the patient line is monitored. In an embodiment, the fluid being drained is monitored using one or more sensors disposed proximate the patient line 130 and/or the drain line 132. In an embodiment, the one or more sensors comprise flow meters (e.g., ultrasonic flow meters). In another embodiment, the one or more sensors comprise at least two pressure transducers configured to measure a pressure differential across a fixed length of tubing. In yet other embodiments, the one or more sensors comprise at least one load cell configured to measure a mass of fluid drained from the patient line to indirectly estimate a volume of fluid drained from the patient line. After the measurement using the load cell(s), the fluid can be drained to the drain line.

At step 1612, once the amount of fluid to be drained has been reached, the controller determines whether another PD cycle is initiated. In an embodiment, a patient may undergo multiple PD cycles during a treatment session. If another PD cycle is to be performed, then steps 1602-1610 can be repeated. However, if no other PD cycles are to be started during this session, or if an amount of fluid drained from the patient is significantly less than the amount of fluid that was introduced into the patient's abdominal cavity, thereby indicating a potential issue during the drain phase of the PD cycle, then the treatment can terminate.

In an embodiment, the PD machine (e.g., a controller, a processor, etc.) is configured to generate an alert when a difference in the amount of fluid transferred to the patient line during the fill phase and the amount of fluid transferred from the patient line to the drain line during the drain phase is above a threshold value. The threshold value can be set as a fixed amount or as a percentage of the amount of fluid transferred to the patient line during the fill phase.

Figure 17:
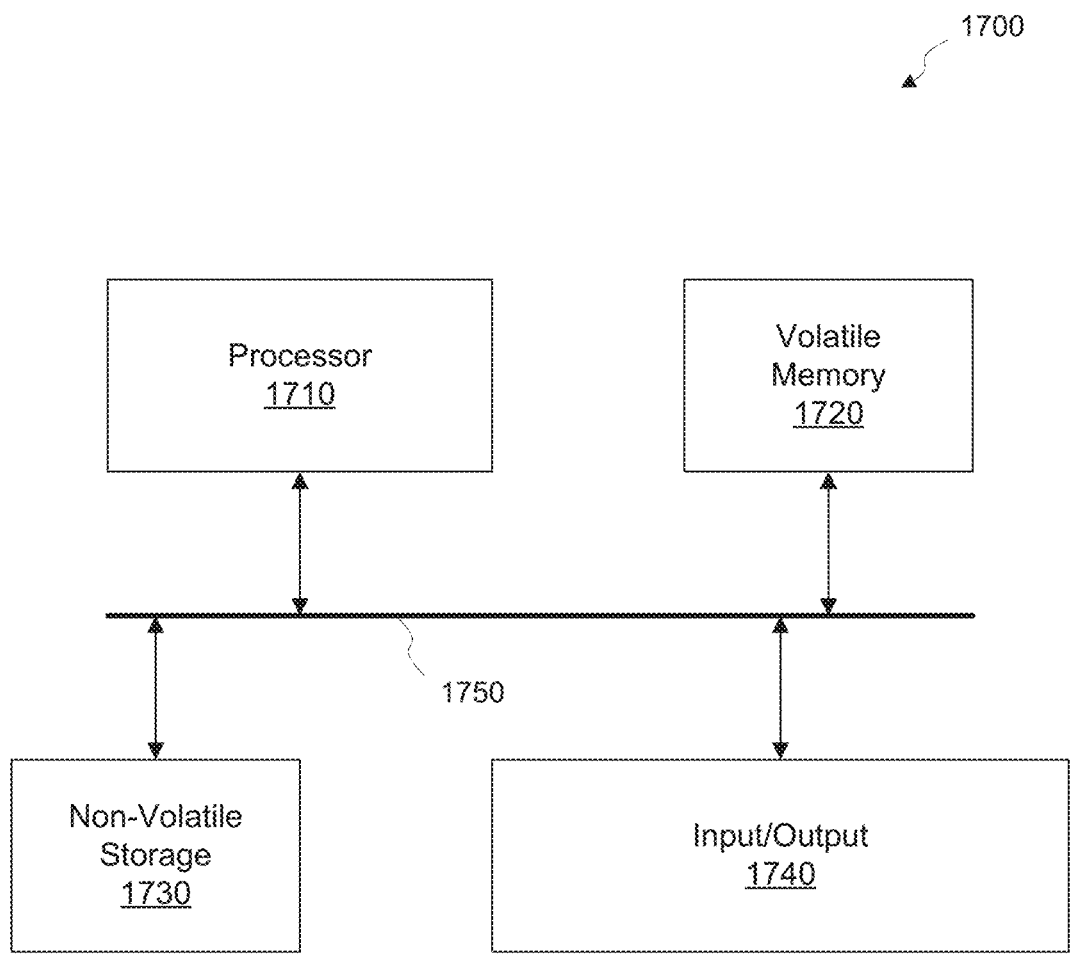
FIG. 17 illustrates an exemplary computer system, in accordance with some embodiments.

FIG. 17 illustrates an exemplary computer system 1700, in accordance with some embodiments. It will be appreciated that, in various embodiments, the control unit 139 can be implemented, at least in part, to include the components of the computer system 1700. The processor 1710 can execute instructions that cause the computer system 1700 to implement the functionality of the control unit 139, as described above.

As depicted in FIG. 17, the system 1700 includes a processor 1710, a volatile memory 1720, a non-volatile storage 1730, and one or more input/output (I/O) devices 1740. Each of the components 1710, 1720, 1730, and 1740 can be interconnected, for example, using a system bus 1750 to enable communications between the components. The processor 1710 is capable of processing instructions for execution within the system 1700. The processor 1710 can be a single-threaded processor, a multi-threaded processor, a vector processor that implements a single-instruction, multiple data (SIMD) architecture, a quantum processor, or the like. The processor 1710 is capable of processing instruction stored in the volatile memory 1720. In some embodiments, the volatile memory 1720 is a dynamic random access memory (DRAM). The instructions can be loaded into the volatile memory 1720 from the non-volatile storage 1730. In some embodiments, the non-volatile storage 1730 can comprise a flash memory such as an EEPROM. In other embodiments, the non-volatile storage 1730 can comprise a hard disk drive (HDD), solid state drive (SSD), or other types of non-volatile media. The processor 1710 is configured to execute the instructions, which cause the PD machine 102 to carry out the various functionality described above.

In some embodiments, the memory 1720 stores information for operation of the PD machine 102. For example, the operating parameters can be stored in the memory 1720. The processor 1710 can read the values of the operating parameters from the memory 1720 and then adjust the operation of the PD machine 102 accordingly. For example, a speed of the pistons 133A, 133B can be stored in or written to the memory 1720 and read from the memory 1720. The speed is then used to control signals transmitted to the stepper motor drivers.

The I/O device(s) 1740 provides input and/or output interfaces for the system 1700. In some embodiments, the I/O device(s) 1740 include a network interface controller (NIC) that enables the system 1700 to communicate with other devices over a network, such as a local area network (LAN) or a wide area network (WAN) such as the Internet. In some embodiments, the non-volatile storage 1730 can include both local and remote computer readable media. The remote computer readable media can refer to a network storage device such as a storage area network (SAN) or a cloud-based storage service. The I/O device(s) 1740 can also include, but are not limited to, a serial communication device (e.g., RS-232 port, USB host, etc.), a wireless interface device (e.g., a transceiver conforming to Wi-Fi or cellular communication protocols), a sensor interface controller, a video controller (e.g., a graphics card), or the like.

It will be appreciated that the system 1700 is merely one exemplary computer architecture and that the control unit 139 or other processing devices can include various modifications such as additional components in lieu of or in addition to the components shown in FIG. 17. For example, in some embodiments, the control unit 139 can be implemented as a system-on-chip (SoC) that includes a primary integrated circuit die containing one or more CPU core, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). The chip can be included in a chipset that includes additional chips providing the I/O device 1740 functionality when connected to the SoC via a printed circuit board.

The system and techniques described herein are discussed for illustrative purposes principally in connection with a particular type of PD cycler, for example a PD cycler having piston-based pumps and a heater tray used to batch heat dialysate in a heater bag. It is noted that the system and techniques described herein may be suitably used in connection with other types and configurations of dialysis machines involving the transmission of fluid to and from a patient via a patient line and for which patient line checks and occlusion detection would be beneficially performed. For example, the system and techniques described herein may be used in connection with a PD cycler using a different configuration and style of pump, such as a peristaltic pump, and may be used in connection with other types of dialysate heating arrangements, such as in-line heating arrangements.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A peritoneal dialysis (PD) system, comprising:
a patient line;
a drain line;
a pump;
one or more sensors; and
a processor configured to:
engage the pump to pump dialysate through the patient line during a fill phase of a PD cycle;
pump fluid from the patient line to the drain line during a drain phase of the PD cycle; and
disengage the pump during at least a portion of the drain phase of the PD cycle, wherein the patient line is shunted to the drain line to allow the fluid to bypass the pump during the at least the portion of the drain phase of the PD cycle, wherein a distal end of the drain line is connected to a drain or drain receptacle, and wherein disengaging the pump during the drain phase allows the fluid to drain naturally from the patient line to the drain or drain receptacle through the drain line without the use of any pumping mechanism.

2. The PD system of claim 1, wherein the pump comprises one or more pistons configured to engage with one or more corresponding pump chambers formed in a disposable cassette connected to the patient line and the drain line.

3. The PD system of claim 2, wherein disengaging the pump comprises configuring one or more valves of the cassette to form a fluid path in the cassette that connects the patient line to the drain line, and wherein the fluid path does not include any of the one or more pump chambers.

4. The PD system of claim 1, wherein the pump comprises a peristaltic pump.

5. The PD system of claim 4, wherein disengaging the pump comprises moving a roller assembly of the peristaltic pump away from a fixed surface such that a flexible tube between the roller assembly and the fixed surface is not contacted by the roller assembly.

6. The PD system of claim 1, wherein disengaging the pump comprises opening a bypass valve to allow fluid to flow from the patient line to the drain line.

7. The PD system of claim 1, wherein the one or more sensors comprise a flow meter.

8. The PD system of claim 1, wherein the one or more sensors comprise at least two pressure transducers configured to measure a pressure differential across a fixed length of tubing.

9. The PD system of claim 1, wherein the processor is further configured to:
monitor, based on signals from the one or more sensors, an amount of fluid transferred to the patient line during the fill phase;
monitor, based on signals from the one or more sensors, an amount of fluid transferred from the patient line to the drain line during the drain phase; and
generate an alert when a difference in the amount of fluid transferred to the patient line during the fill phase and the amount of fluid transferred from the patient line to the drain line during the drain phase is above a threshold value.

10. The PD system of claim 9, wherein the processor is further configured to disengage the pump responsive to the alert.

11. A method of operating a peritoneal dialysis (PD) machine, the method comprising:
engaging a pump during a fill phase of a PD cycle;
monitoring, using one or more sensors, an amount of fluid transferred to a patient line during the fill phase;
after a dwell period has elapsed, pump the fluid from the patient line to a drain line to begin a drain phase of the PD cycle;
disengaging, via a processor, the pump during at least a portion of the drain phase of the PD cycle, wherein the patient line is shunted to the drain line to allow the fluid to bypass the pump during the at least the portion of the drain phase of the PD cycle; and
monitoring, using the one or more flow sensors, an amount of fluid transferred from the patient line to the drain line during the drain phase,
wherein a distal end of the drain line is connected to a drain or drain receptacle, and wherein disengaging the pump during the drain phase of the PD cycle allows the fluid to drain naturally from the patient line to the drain or drain receptacle through the drain line without the use of any pumping mechanism.

12. The method of claim 11, wherein the pump comprises one or more pistons configured to engage with one or more corresponding pump chambers formed in a disposable cassette connected to the patient line and the drain line.

13. The method of claim 12, wherein disengaging the pump comprises configuring one or more valves of the cassette to form a fluid path in the cassette that connects the patient line to the drain line, and wherein the fluid path does not include any of the one or more pump chambers.

14. The method of claim 11, wherein the pump comprises a peristaltic pump.

15. The method of claim 14, wherein disengaging the pump comprises moving a roller assembly of the peristaltic pump away from a fixed surface such that a flexible tube between the roller assembly and the fixed surface is not contacted by the roller assembly.

16. The method of claim 11, wherein the one or more sensors comprise at least one of:
a flow meter;
at least two pressure transducers configured to measure a pressure differential across a fixed length of tubing; or
at least one load cell configured to measure a mass of fluid.

17. A non-transitory computer readable storage medium storing instructions that, when executed by a processor, causes a peritoneal dialysis (PD) machine to operate in a hybrid mode by performing steps comprising:
engaging a pump during a fill phase of a PD cycle;
monitoring an amount of fluid transferred to a patient line during the fill phase;
after a dwell period has elapsed, pump the fluid from the patient line to a drain line to begin a drain phase of the PD cycle;
disengaging, via the processor, the pump during at least a portion of the drain phase of the PD cycle, wherein the patient line is shunted to a drain line to allow the fluid to bypass the pump during the at least the portion of the drain phase of the PD cycle; and
monitoring the amount of the fluid transferred from the patient line to the drain line during the drain phase,
wherein a distal end of the drain line is connected to a drain or drain receptacle, and wherein disengaging the pump during the drain phase allows the fluid to drain naturally from the patient line to the drain or drain receptacle through the drain line without the use of any pumping mechanism.

18. The non-transitory computer readable storage medium of claim 17, wherein the pump comprises one or more pistons configured to engage with one or more corresponding pump chambers formed in a disposable cassette connected to the patient line and the drain line.

19. The non-transitory computer readable storage medium of claim 18, wherein disengaging the pump comprises configuring one or more valves of the cassette to form a fluid path in the cassette that connects the patient line to the drain line, and wherein the fluid path does not include any of the one or more pump chambers.

20. The non-transitory computer readable storage medium of claim 17, wherein the pump comprises a peristaltic pump.

21. The PD system of claim 1, wherein disengaging the pump, by the processor, is manually configured by a user.

22. The PD system of claim 1, wherein disengaging the pump, by the processor, is automatically configured in response to an alarm generated from monitoring by the one or more sensors.

* * * * *